(12) United States Patent
Deak et al.

(10) Patent No.: US 12,055,605 B2
(45) Date of Patent: Aug. 6, 2024

(54) HYDROGEN GAS SENSOR UTILIZING ELECTRICALLY ISOLATED TUNNELING MAGNETORESISTIVE SENSING ELEMENTS

(71) Applicant: MultiDimension Technology Co., Ltd., Zhangjiagang (CN)

(72) Inventors: James Geza Deak, Zhangjiagang (CN); Zhimin Zhou, Zhangjiagang (CN)

(73) Assignee: MultiDimension Technology Co., Ltd., Zhangjiagang (CN)

( * ) Notice: Subject to any disclaimer, the term of this patent is extended or adjusted under 35 U.S.C. 154(b) by 327 days.

(21) Appl. No.: 17/753,360

(22) PCT Filed: Aug. 18, 2020

(86) PCT No.: PCT/CN2020/109816
§ 371 (c)(1),
(2) Date: Jul. 15, 2022

(87) PCT Pub. No.: WO2021/036867
PCT Pub. Date: Mar. 4, 2021

(65) Prior Publication Data
US 2022/0342012 A1 Oct. 27, 2022

(30) Foreign Application Priority Data
Aug. 30, 2019 (CN) .......................... 201910817744.5

(51) Int. Cl.
*G01R 33/05* (2006.01)
*G01N 33/00* (2006.01)
*G01R 33/09* (2006.01)

(52) U.S. Cl.
CPC ......... *G01R 33/098* (2013.01); *G01N 33/005* (2013.01)

(58) Field of Classification Search
CPC ................ G01R 33/00; G01R 33/0035; G01R 33/0023; G01R 33/0017; G01R 31/3191;
(Continued)

(56) References Cited

U.S. PATENT DOCUMENTS 6,006,582 A * 12/1999 Bhandari ............. G01N 21/783
73/31.06
11,137,452 B2 * 10/2021 Deak .................. G01R 33/0011
(Continued)

FOREIGN PATENT DOCUMENTS

| CN | 103558253 A | 2/2014 |
|---|---|---|
| CN | 104677952 A | 6/2015 |

(Continued)

OTHER PUBLICATIONS

"International Application No. PCT/CN2020/109816, International Search Report and Written Opinion mailed Nov. 20, 2020", (Nov. 20, 2020), 12 pgs.

*Primary Examiner* — Jermele M Hollington
*Assistant Examiner* — Taqi R Nasir
(74) *Attorney, Agent, or Firm* — Schwegman Lundberg & Woessner, P.A.

(57) ABSTRACT

A hydrogen gas sensor utilizing electrically isolated tunneling magnetoresistive sensing elements is provided. The hydrogen gas sensor comprises: a substrate in an X-Y plane, tunneling magnetoresistive sensors located on the substrate, and a hydrogen sensing layer located on the tunnel magnetoresistive sensors. The hydrogen sensing layer and the tunneling magnetoresistive sensor are electrically isolated from each other. The hydrogen sensing layer includes a multi-layer thin film structure formed from palladium layers and ferromagnetic layers, wherein the palladium layers are used for absorbing hydrogen in the air that causes a change in the orientation angle of a magnetic anisotropy field in each of the ferromagnetic layers in the X-Z plane into an
(Continued)

X-axis direction. The tunnel magnetoresistive sensors are used for detecting a magnetic field signal of the hydrogen sensing layer, wherein the magnetic signal determines the hydrogen gas concentration. This hydrogen gas sensor ensures measurement safety.

13 Claims, 17 Drawing Sheets

(58) Field of Classification Search
CPC ...... G01R 33/098; G01B 7/004; G01C 17/38; G06F 3/017; G06F 3/0346; G06F 3/012; G01N 33/005
See application file for complete search history.

(56) References Cited

U.S. PATENT DOCUMENTS

| | | | |
|---|---|---|---|
| 2002/0017126 A1 | 2/2002 | Dimeo et al. | |
| 2003/0153088 A1* | 8/2003 | DiMeo, Jr. ........... | G01N 27/128 73/31.05 |
| 2018/0328902 A1 | 11/2018 | Tseng et al. | |

FOREIGN PATENT DOCUMENTS

| | | |
|---|---|---|
| CN | 109211984 A | 1/2019 |
| CN | 109283228 A | 1/2019 |
| CN | 110412118 A | 11/2019 |
| CN | 210572104 U | 5/2020 |
| TW | 201901147 A | 1/2019 |
| WO | WO-2021036867 A1 | 3/2021 |

\* cited by examiner

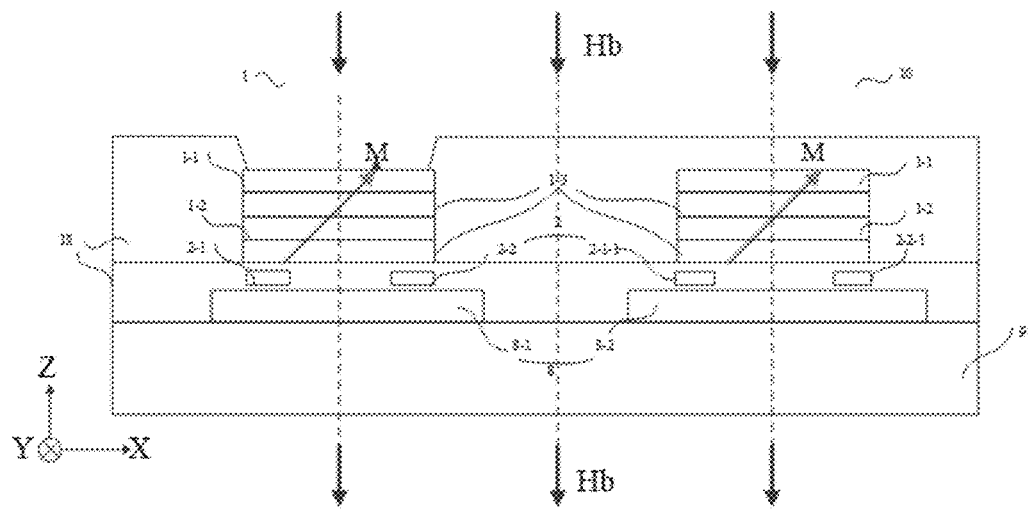
FIG. 1
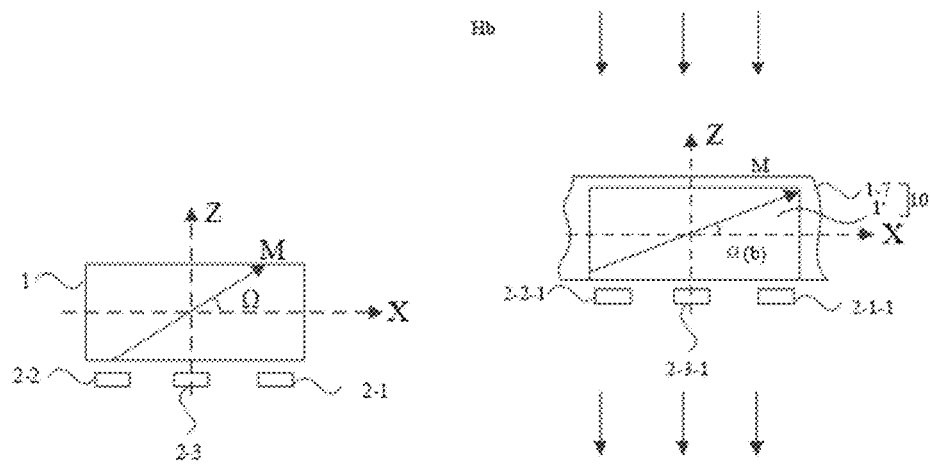
FIG. 2  FIG. 3
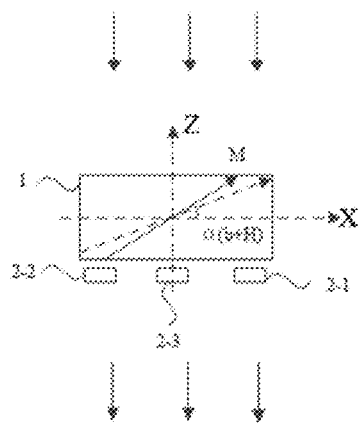
FIG. 4

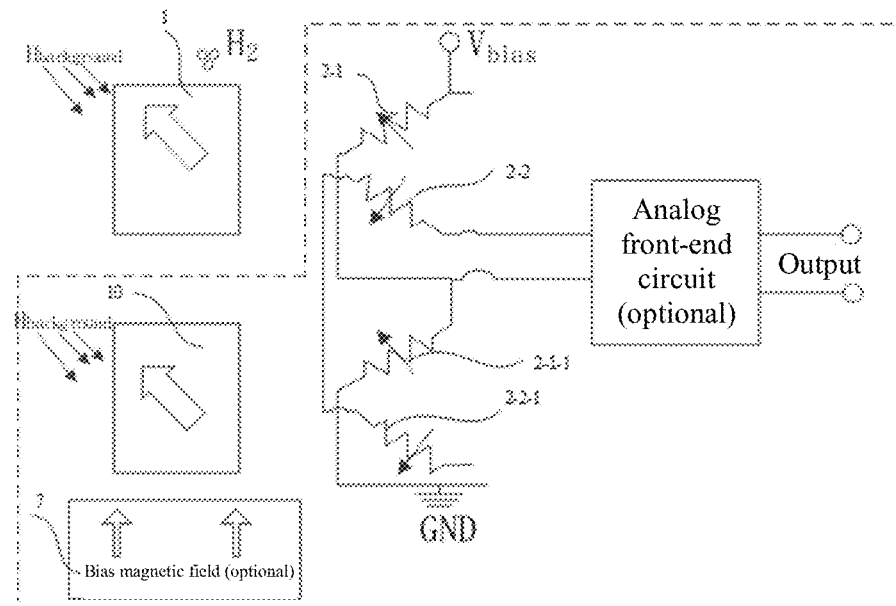
FIG. 22
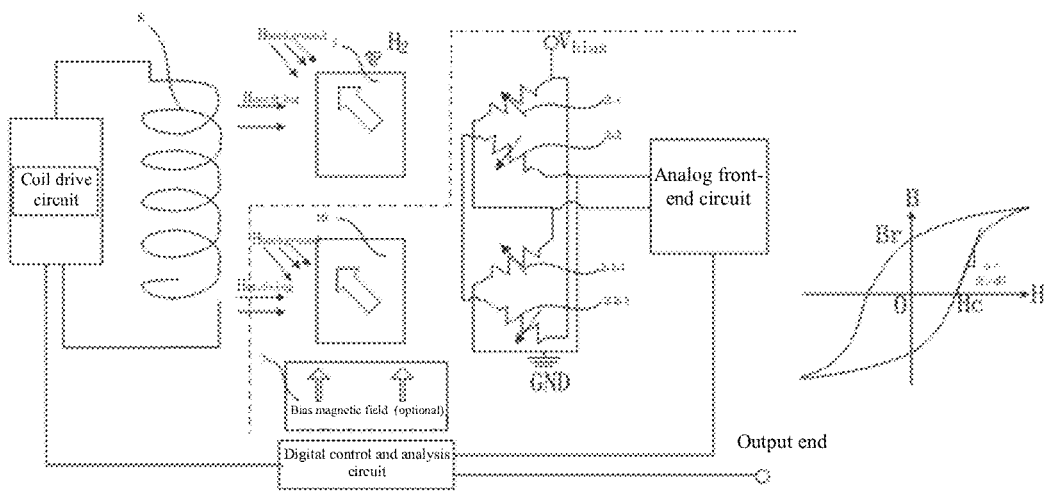
FIG. 23a  FIG. 23b
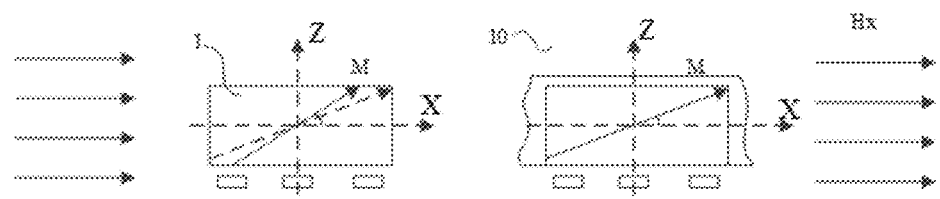
FIG. 24a

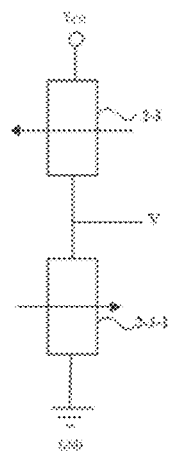 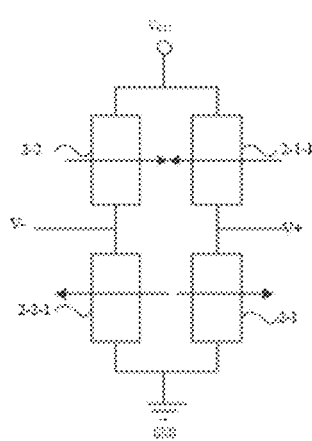
FIG. 31a  FIG. 31b
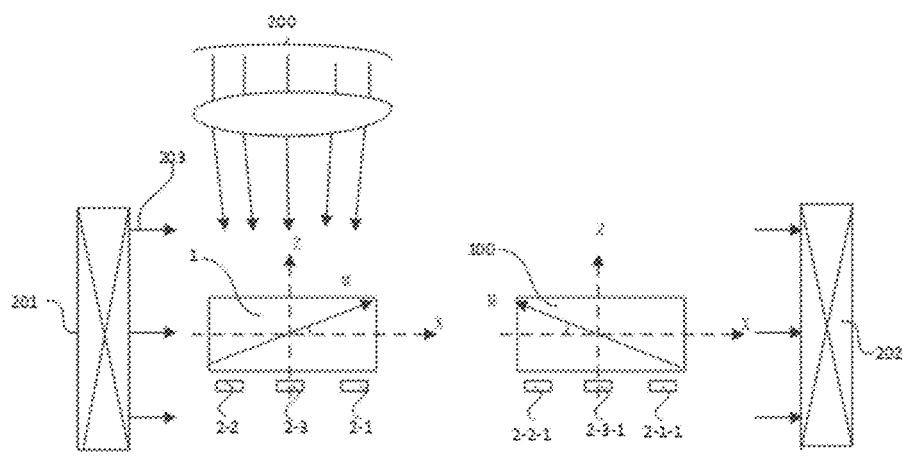
FIG. 32a
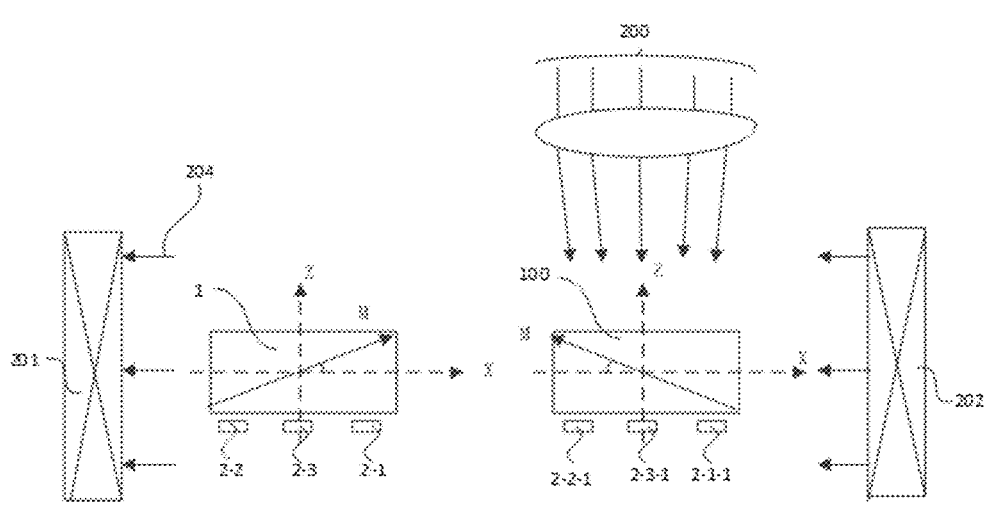
FIG. 32b

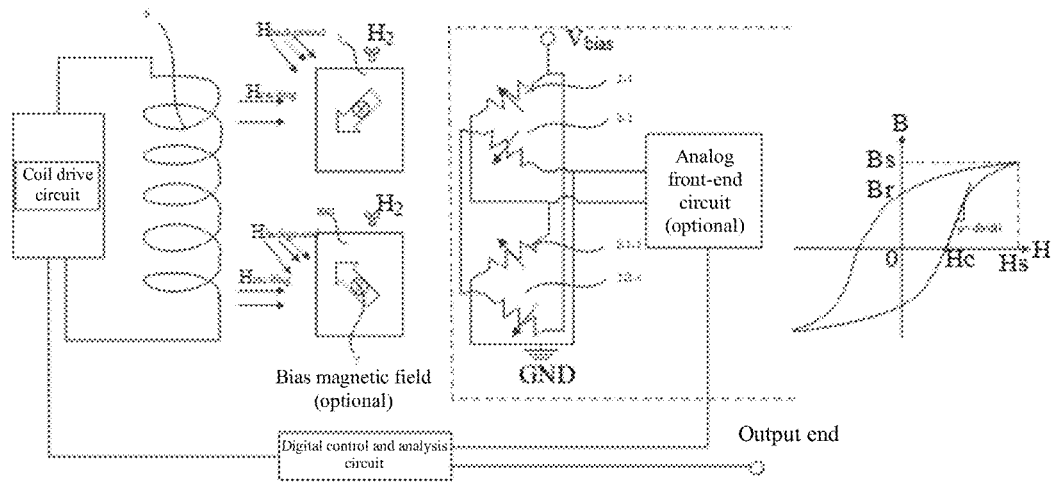
FIG. 43a  FIG. 43b
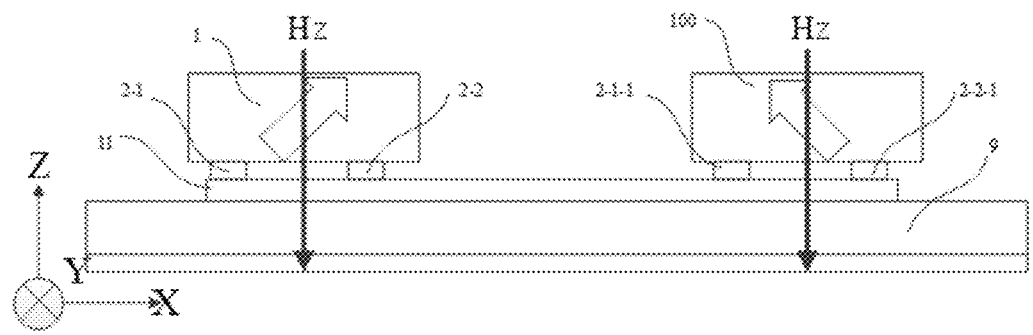
FIG. 44a
FIG. 44b

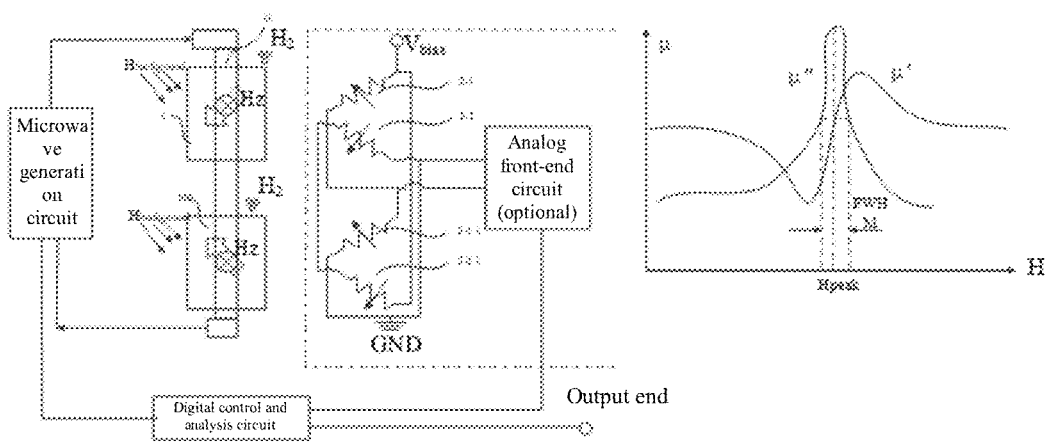
FIG. 45a  FIG. 45b
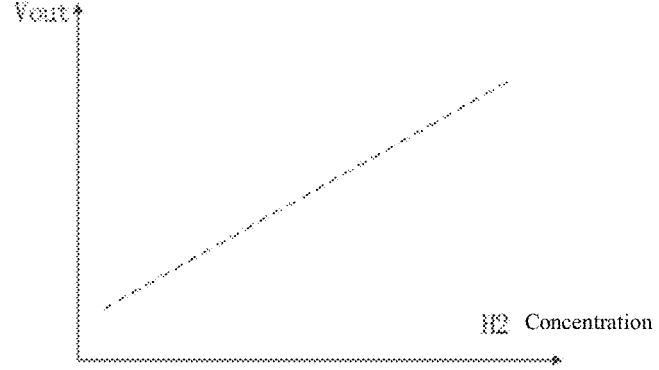
FIG. 46

HYDROGEN GAS SENSOR UTILIZING ELECTRICALLY ISOLATED TUNNELING MAGNETORESISTIVE SENSING ELEMENTS

PRIORITY CLAIM TO RELATED APPLICATIONS

This application is a U.S. national stage filing under 35 U.S.C. § 371 from International Application No. PCT/CN2020/109816, filed on 18 Aug. 2020, which claims priority to Chinese Application No. 201910817744.5, filed on 30 Aug. 2019. This application incorporates by reference the entirety of International Application No. PCT/CN2020/109816 and its published version WO 2021/036867 (published 4 Mar. 2021).

TECHNICAL FIELD

The present disclosure relates to the technical field of gas sensors, and in particular, to a hydrogen gas sensor utilizing electrically isolated tunneling magnetoresistive sensing elements.

BACKGROUND ART

As a renewable, hazardous emission-free new energy source to replace fossil fuel energy, hydrogen gas has attracted increasingly more attention worldwide in recent years and has developed rapidly. At present, the world's major economies, such as the United States, the European Union, and Japan, are sparing no effort to explore hydrogen gas as a new energy and new fuel for future vehicles and households.

Hydrogen gas cannot be sensed by human senses, but it is highly flammable and explosive. A flammability threshold of hydrogen gas in air is around 4%. In order to ensure the safety of a device using hydrogen gas as an energy source, a reliable and highly sensitive hydrogen gas sensor is required to detect the hydrogen gas concentration.

There are many types of conventional hydrogen gas sensors. For example, an optical sensor utilizing surface plasmon resonance can monitor a peak position and intensity change of a surface plasmon resonance peak of a surface reflected light spectrum of a metal nanorod array through a spectrometer, thus realizing real-time sensing of hydrogen gas in an environment. For example, a resistive thin-film hydrogen gas sensor uses the property of the metal palladium absorbing hydrogen gas, and the purpose of detecting the hydrogen gas concentration can be achieved by detecting changes in a resistance value of the metal palladium.

However, when existing hydrogen gas sensors are actually working, sensing units all need to have electric currents passing through. If the hydrogen gas concentration in the air reaches an explosion limit, circuits in the sensing units may ignite the hydrogen gas and cause an explosion.

SUMMARY OF THE INVENTION

In order to solve the deficiencies in the above technologies, an embodiment of the present disclosure proposes a hydrogen gas sensor utilizing electrically isolated tunneling magnetoresistive sensing elements, including:

a substrate in an X-Y plane, tunneling magnetoresistive sensors located on the substrate, and a hydrogen sensing layer located on the tunneling magnetoresistive sensors, the hydrogen sensing layer and the tunneling magnetoresistive sensor being electrically isolated from each other, and the hydrogen sensing layer including a multi-layer thin film structure of [palladium layer/ferromagnetic layer]n, where n is an integer greater than or equal to 1; and the palladium layers being used for adsorbing hydrogen in the air that causes a change in the orientation angle of a magnetic anisotropy field in each of the ferromagnetic layers along an X-axis direction in the X-Z plane, and the tunneling magnetoresistive sensors being used for detecting a magnetic field signal of the hydrogen sensing layer, where the magnetic signal determines the hydrogen gas concentration.

In the disclosed embodiment, electrical isolation is adopted between the hydrogen sensing layer and the tunneling magnetoresistive sensor. The hydrogen sensing layer absorbs hydrogen gas and generates a corresponding change in the orientation angle. The tunneling magnetoresistive sensors acquire a magnetic field signal to detect the hydrogen gas concentration. In the embodiment of the present disclosure, no electric current or voltage will pass through the hydrogen sensing layer, and therefore, even if the hydrogen gas concentration in the air reaches an explosion limit, the hydrogen sensing layer will not cause an explosion. The hydrogen sensing layer and the tunneling magnetoresistive sensor are electrically isolated, the electric current or voltage in the tunneling magnetoresistive sensor will not react with the hydrogen gas in the air through the hydrogen sensing layer, and the tunneling magnetoresistive sensor will not ignite the hydrogen gas and cause an explosion. Compared with the prior art, test security is guaranteed.

BRIEF DESCRIPTION OF THE DRAWINGS

FIG. 1 is a schematic diagram of a hydrogen gas sensor according to an embodiment of the present disclosure;

FIG. 2 is a schematic diagram of an orientation angle of a magnetic anisotropy field of a hydrogen sensing layer according to an embodiment of the present disclosure;

FIG. 3 is a schematic diagram of a positional relationship between a non-hydrogen sensing layer and a reference magnetoresistive sensing unit string according to an embodiment of the present disclosure;

FIG. 4 is a schematic diagram of a positional relationship between a hydrogen sensing layer and a magnetoresistive sensing unit string according to an embodiment of the present disclosure;

FIG. 22 is a schematic diagram of hydrogen gas measurement of a static magnetic field reference magnetoresistive sensing unit bridge according to an embodiment of the present disclosure;

FIG. 23a and FIG. 23b are diagrams of hydrogen gas measurement of a bias coil reference magnetoresistive sensing unit bridge according to an embodiment of the present disclosure;

FIG. 24a is a magnetic moment deflection diagram of a bias magnetic field in an X-axis direction according to an embodiment of the present disclosure;

FIG. 31a is a half-bridge structural diagram of a push-pull tunneling magnetoresistive sensor according to an embodiment of the present disclosure;

FIG. 31b is a full-bridge structural diagram of a push-pull tunneling magnetoresistive sensor according to an embodiment of the present disclosure;

FIG. 32a is a schematic diagram of writing a magnetic moment of a push hydrogen sensing layer according to an embodiment of the present disclosure;

FIG. 32b is a schematic diagram of writing a magnetic moment of a pull hydrogen sensing layer according to an embodiment of the present disclosure;

FIG. 43a and FIG. 43b are diagrams of hydrogen gas measurement of an excitation coil push-pull magnetoresistive sensing unit bridge according to an embodiment of the present disclosure;

FIG. 44a is a front view of a push-pull magnetoresistive sensing unit bridge structure including ferromagnetic resonance microstrips according to an embodiment of the present disclosure;

FIG. 44b is a top view of a microwave excitation magnetic field in a Y-axis direction according to an embodiment of the present disclosure;

FIG. 45a and FIG. 45b are diagram of hydrogen gas measurement of a push-pull magnetoresistive sensing unit bridge of a ferromagnetic resonance method according to an embodiment of the present disclosure; and FIG. 46 is a linear relationship diagram between output of a tunneling magnetoresistive sensor and hydrogen gas according to an embodiment of the present disclosure.

DETAILED DESCRIPTION

Figure 5:
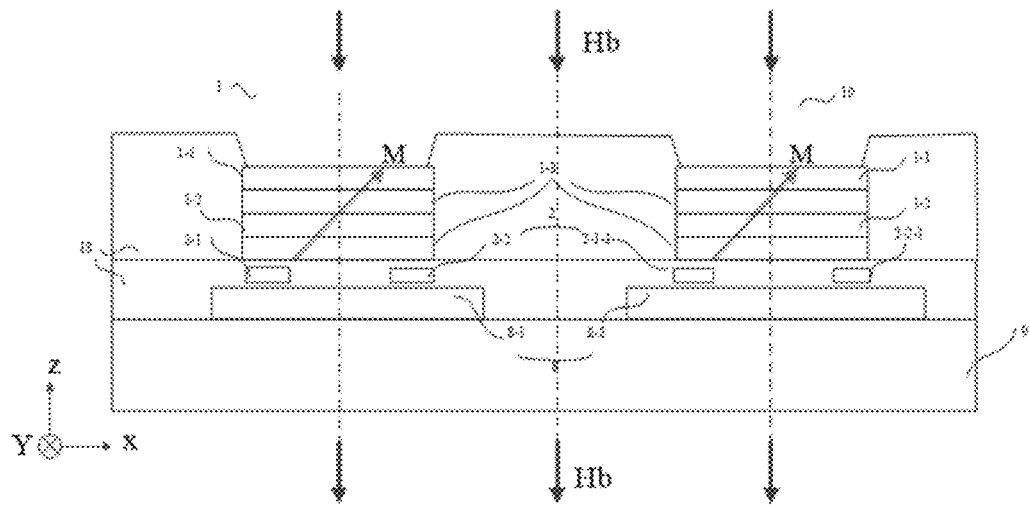
FIG. 5 is a schematic diagram of a hydrogen gas sensor according to an embodiment of the present disclosure.

In order to make the objectives, technical solutions, and advantages of the present disclosure clearer, the technical solutions of the present disclosure will be described clearly and completely through the implementation manners below with reference to the accompanying drawings in the embodiments of the present disclosure. Apparently, the described embodiments are some embodiments but not all embodiments of the present disclosure. Based on the embodiments in the present disclosure, all other embodiments obtained by those of ordinary skill in the art without creative efforts fall within the protection scope of the present disclosure.

Referring to FIG. 1, it is a schematic diagram of a hydrogen gas sensor utilizing electrically isolated tunneling magnetoresistive sensing elements according to an embodiment of the present disclosure. The hydrogen gas sensor provided in this embodiment includes a substrate 9 in an X-Y plane, tunneling magnetoresistive sensors 2 located on the substrate 9, and a hydrogen sensing layer 1 located on the tunneling magnetoresistive sensors 2. The hydrogen sensing layer 1 and the tunneling magnetoresistive sensor 2 are electrically isolated from each other. The hydrogen sensing layer 1 includes a multi-layer thin film structure of [palladium layer/ferromagnetic layer]n, where n is an integer greater than or equal to 1. The palladium layers are used for absorbing hydrogen in the air that causes a change in the orientation angle of a magnetic anisotropy field in each of the ferromagnetic layers along an X-axis direction in the X-Z plane. The tunneling magnetoresistive sensors 2 are used for detecting a magnetic field signal of the hydrogen sensing layer 1, where the magnetic signal determines the hydrogen gas concentration.

In this embodiment, in accordance with an XYZ space coordinate system established by an X-axis, a Y-axis, and a Z-axis perpendicular to one another, a plane parallel to a plane formed by the X-axis and the Y-axis is the X-Y plane, a plane parallel to a plane formed by the X-axis and the Z-axis is the X-Z plane, and a plane parallel to a plane formed by the Z-axis and the Y-axis is a Y-Z plane.

In this embodiment, the hydrogen gas sensor includes the substrate 9, the tunneling magnetoresistive sensor 2, and the hydrogen sensing layer 1. The hydrogen sensing layer 1 and the tunneling magnetoresistive sensor 2 are electrically isolated from each other. It is understandable that an electrical isolation layer 18 is arranged between the hydrogen sensing layer 1 and the tunneling magnetoresistive sensor 2. The electrical isolation layer 18 is located between the hydrogen sensing layer 1 and the tunneling magnetoresistive sensor 2, so as to realize isolation of a hydrogen gas environment and an electric power supply environment to avoid unnecessary explosions.

In this embodiment, the hydrogen sensing layer 1 includes a multi-layer thin film structure of [palladium layer/ferromagnetic layer]n, where n is a positive integer greater than or equal to 1. For example, if n=2, the hydrogen sensing layer 1 includes a 4-layer thin film structure, in which the first and third layers are both ferromagnetic layers and the second and fourth layers are both palladium layers. The palladium layers are used for absorbing hydrogen gas, and therefore, one of the palladium layers in the multi-layer thin film structure of the hydrogen sensing layer 1 is a cap layer for directly contacting with the air and absorbing hydrogen gas, and the remaining palladium layers are intermediate layers and do not directly contact with the air. The palladium layer as the cap layer is denoted as 1-1, the palladium layer as the intermediate layer is denoted as 1-2, the ferromagnetic layer is denoted as 1-3, and the subsequent palladium layers for absorbing hydrogen gas include 1-1 and 1-2. The ferromagnetic layer has a magnetic anisotropy field, and the adsorption of hydrogen gas by the palladium layer will cause a change in the orientation angle of a magnetic anisotropy field in the ferromagnetic layer along the X-axis direction in the X-Z plane.

In this embodiment, the tunneling magnetoresistive sensor 2 can sense the change in the magnetic field of the hydrogen sensing layer 1, and finally realize the measurement of the hydrogen gas concentration according to the change in the magnetic field of the hydrogen sensing layer 1. Specifically, as shown in FIG. 2, under the action of hydrogen gas, a magnetic moment M of the ferromagnetic layer is deflected in the X-Z plane, and the orientation angle along the X-axis direction in the X-Z plane is denoted as Ω. The ferromagnetic layer has a thickness on the nanoscale, and can be regarded as a single domain structure, therefore, the hydrogen sensing layer 1 may be regarded as a magnet with a magnetic moment M, which generates a static magnetic field distribution in the surrounding space. The bottom of the hydrogen sensing layer 1 is provided with the tunneling magnetoresistive sensors 2, which can sense a magnetic field signal of the hydrogen sensing layer 1 to realize the test of the static magnetic field. Then, the orientation angle of the magnetic moment M can be deduced according to the magnetic field signal, and the hydrogen gas concentration may be measured finally according to a corresponding relationship between the orientation angle of the magnetic moment M and the hydrogen gas concentration.

In this embodiment, electrical isolation is adopted between the hydrogen sensing layer and the tunneling magnetoresistive sensor. The hydrogen sensing layer absorbs hydrogen gas and generates a corresponding change in the orientation angle, and the tunneling magnetoresistive sensor acquires the magnetic field signal to detect the hydrogen gas concentration. In this embodiment, no electric current or voltage will pass through the hydrogen sensing layer, and therefore, even if the hydrogen gas concentration in the air reaches an explosion limit, the hydrogen sensing layer in contact with the air will not cause an explosion. Due to the electrical isolation between the hydrogen sensing layer and the tunneling magnetoresistive sensor, the electric current or voltage in the tunneling magnetoresistive sensor will not react with the hydrogen gas in the air through the hydrogen sensing layer, and therefore, the tunneling magnetoresistive sensor is also unlikely to ignite the hydrogen gas and cause an explosion. Compared with the prior art, test security is guaranteed.

For example, on the basis of the above technical solution, an optional hydrogen gas sensor further includes: a non-hydrogen sensing layer 10. The non-hydrogen sensing layer 10 is located on the tunneling magnetoresistive sensor 2. The hydrogen sensing layer 1, the non-hydrogen sensing layer 10, and the tunneling magnetoresistive sensor 2 are electrically isolated from each other. The non-hydrogen sensing layer 10 is a multi-layer thin film structure of [non-palladium layer/ferromagnetic layer]n, or the non-hydrogen sensing layer 10 includes a multi-layer thin film structure of [palladium layer/ferromagnetic layer]n and a passivation layer covering the multi-layer thin film structure.

In this embodiment, the electrical isolation layer 18 is located between the hydrogen sensing layer 1, the non-hydrogen sensing layer 10, and the tunneling magnetoresistive sensor 2, so as to realize the isolation between the hydrogen gas environment and the electric power supply environment of the tunneling magnetoresistive sensor to avoid unnecessary explosions. The hydrogen gas sensor is in a background magnetic field generated by the environment during actual operation, for example, due to the background magnetic field generated by an electric power line, the background magnetic field Hb will also have an additional deflection effect on the orientation angle of the magnetic moment M of the hydrogen sensing layer 1; therefore, it needs to eliminate the influence of the background magnetic field Hb on the hydrogen sensing layer 1.

As shown in FIG. 1, the optional hydrogen sensing layer 1 and the non-hydrogen sensing layer 10 both include a multi-layer thin film structure of [palladium layer/ferromagnetic layer]n, and the non-hydrogen sensing layer 10 further includes a passivation layer covering the multi-layer thin film structure of [palladium layer/ferromagnetic layer]n. In this embodiment, the non-hydrogen sensing layer 10 includes a multi-layer thin film structure of [palladium layer/ferromagnetic layer]n, and therefore, the non-hydrogen sensing layer 10 provides the change in the magnetic moment orientation angle caused by the background magnetic field. It is understandable that the hydrogen sensing layer 1 also reflects the change in the magnetic moment orientation angle caused by the background magnetic field when hydrogen gas is not absorbed.

In order to eliminate the background magnetic field, the non-hydrogen sensing layer 10 further includes a passivation layer covering the multi-layer thin film structure of [palladium layer/ferromagnetic layer]n. The passivation layer isolates the palladium layer in the non-hydrogen sensing layer 10 from contacting with the hydrogen gas in the air, thus preventing the non-hydrogen sensing layer 10 from absorbing the hydrogen gas. Therefore, the orientation angle of the magnetic moment M represented by the ferromagnetic layer of the non-hydrogen sensing layer 10 is not related to hydrogen gas, but only to the background magnetic field Hb. The palladium layer of the hydrogen sensing layer 1 is in contact with hydrogen gas, and the hydrogen sensing layer 1 provides the change in the magnetic moment orientation angle caused by the background magnetic field and the hydrogen gas. In this way, the tunneling magnetoresistive sensors 2 are used for detecting the magnetic field signal of the hydrogen sensing layer 1 and the magnetic field signal of the non-hydrogen sensing layer 10 to obtain a variation in a magnetic field of the hydrogen sensing layer 1 caused by absorbing hydrogen gas and a variation in a magnetic field of the non-hydrogen sensing layer 10 caused by the background magnetic field. The hydrogen gas concentration information is determined according to the variations in the two magnetic field, and the influence of the background magnetic field on the hydrogen gas concentration is removed, thereby improving the detection accuracy.

FIG. 3 is a schematic diagram of the magnetic field of the non-hydrogen sensing layer. The non-hydrogen sensing layer 10 includes a passivation layer 1-7. The passivation layer 1-7 isolates hydrogen gas and the multi-layer thin film structure 1' of [palladium layer/ferromagnetic layer]n, so that the non-hydrogen sensing layer 10 will not react with the hydrogen gas. In this case, the ferromagnetic layer of the non-hydrogen sensing layer 10 provides a magnetic anisotropy field with an orientation angle b, that is, the orientation angle of the ferromagnetic layer caused by the background magnetic field is $\Omega(b)$, which is not affected by hydrogen gas. An optional material of the passivation layer 1-7 may be photoresist, $Al_2O_3$, SiN, $SiO_2$, or SiC.

FIG. 4 is a schematic diagram of the magnetic field of the hydrogen sensing layer. The palladium layer of the hydrogen sensing layer 1 adsorbs hydrogen gas, which causes the change in the orientation angle of the magnetic moment of the ferromagnetic layer. At the same time, the background magnetic field also causes the change in the orientation angle of the magnetic moment of the ferromagnetic layer, and finally the orientation angle of the ferromagnetic layer is $\Omega(b+H)$, where H is the change in the magnetic anisotropy field of the ferromagnetic layer caused by the hydrogen gas factor. Based on this, the tunneling magnetoresistive sensor 2 can eliminate the background magnetic field signal according to the signal of the background magnetic field and the signal of the magnetic field affected by hydrogen gas, and then calculates the hydrogen gas concentration. The hydrogen gas concentration is not affected by the background magnetic field, which improves the test accuracy and has high sensitivity.

As shown in FIG. 5, the optional non-hydrogen sensing layer 10 is a multi-layer thin film structure of [non-palladium layer/ferromagnetic layer]n. In this embodiment, the optional non-palladium layer is a copper layer, a titanium layer, or a tantalum layer, and none of the metals in the non-palladium layer can absorb hydrogen gas; therefore, the orientation angle of the magnetic moment of the non-hydrogen sensing layer 10 is only influenced by the background magnetic field. The non-palladium layer can come into contact with air. It is understandable that when the hydrogen sensing layer 1 does not absorb hydrogen gas, it also reflects the change in the orientation angle of the magnetic moment caused by the background magnetic field. In this embodiment, the non-palladium layer can prevent the non-hydrogen sensing layer 10 from absorbing hydrogen gas, so the tunneling magnetoresistive sensors 2 are used for detecting the magnetic field signal of the hydrogen sensing layer 1 and the magnetic field signal of the non-hydrogen sensing layer 10 to obtain the variation in the magnetic field of the hydrogen sensing layer 1 caused by the absorption of hydrogen gas. The hydrogen gas concentration information is determined according to the variation in the magnetic field. In this way, the influence of the background magnetic field on the hydrogen gas concentration is removed, thereby improving the detection accuracy.

Figure 6:
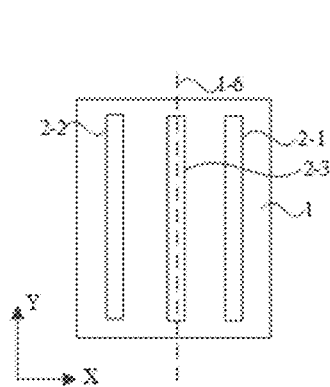
FIG. 6 is a top view of a hydrogen sensing layer and a magnetoresistive sensing unit string according to an embodiment of the present disclosure.
Figure 7:
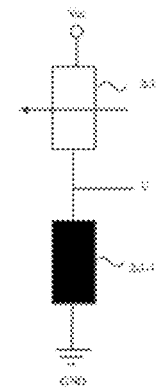
FIG. 7 is a reference half-bridge structural diagram of a tunneling magnetoresistive sensor according to an embodiment of the present disclosure.
Figure 8:
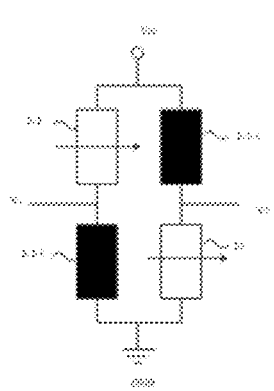
FIG. 8 is a reference full-bridge structural diagram of a tunneling magnetoresistive sensor according to an embodiment of the present disclosure.

As shown in FIG. 6 to FIG. 8, the optional tunneling magnetoresistive sensor 2 is a referenced bridge sensor. The tunneling magnetoresistive sensor 2 includes a sensitive bridge arm and a reference bridge arm, the sensitive bridge arm includes a magnetoresistive sensing unit string, and the reference bridge arm includes a reference magnetoresistive sensing unit string. Magnetic field sensitive directions of the magnetoresistive sensing unit string and the reference magnetoresistive sensing unit string are both the X-axis direction. The hydrogen sensing layer 1 and the non-hydrogen sensing layer 10 are both strip shaped, a long axis of the strip is the Y-axis direction, and a short axis of the strip is the X-axis direction. In the X-Y plane, an orthographic projection of the magnetoresistive sensing unit string is located on a Y-axis centerline within the strip of the hydrogen sensing layer, and/or, an orthographic projection of the magnetoresistive sensing unit string is located at the same positions on both sides of the Y-axis centerline within the strip of the hydrogen sensing layer. In the X-Y plane, an orthographic projection of the reference magnetoresistive sensing unit string is located on a Y-axis centerline within the strip of the non-hydrogen sensing layer, and/or an orthographic projection of the reference magnetoresistive sensing unit string is located at the same positions on both sides of the Y-axis centerline within the strip of the non-hydrogen sensing layer. The magnetoresistive sensing unit string and the reference magnetoresistive sensing unit string are arranged in the same way. The hydrogen sensing layer is magnetically coupled to the sensitive bridge arm and magnetically isolated from the reference bridge arm. The non-hydrogen sensing layer is magnetically isolated from the sensitive bridge arm and magnetically coupled to the reference bridge arm.

As shown in FIG. 1 to FIG. 5, the tunneling magnetoresistive sensor 2 includes a sensitive bridge arm and a reference bridge arm, the sensitive bridge arm includes a magnetoresistive sensing unit string, and the reference bridge arm includes a reference magnetoresistive sensing unit string. The magnetoresistive sensing unit string includes magnetoresistive sensing units 2-1, 2-2, and 2-3, and the reference magnetoresistive sensing unit string includes reference magnetoresistive sensing units 2-1-1, 2-2-1, and 2-3-1. The magnetoresistive sensing unit string is located between the substrate 9 and the hydrogen sensing layer 1, and the reference magnetoresistive sensing unit string is located between the substrate 9 and the non-hydrogen sensing layer 10.

As shown in FIG. 6, the hydrogen sensing layer 1 and the non-hydrogen sensing layer 10 are both strip shaped, a long axis of the strip is the Y-axis direction, and a short axis of the strip is the X-axis direction. Specifically, a plane where the hydrogen sensing layer 1 and the non-hydrogen sensing layer 10 are located is the X-Y plane, and is strip shaped. A long-side extension direction of the strip shape of the X-Y plane, i.e., the long-axis direction, is the Y-axis direction, and a short-side extending direction, i.e., the short-axis direction, is the X-axis direction. Here, magnetic field sensitive directions of the magnetoresistive sensing unit string and the reference magnetoresistive sensing unit string are both the X-axis direction. Only a relative positional relationship between the hydrogen sensing layer 1 and the magnetoresistive sensing unit string is shown in FIG. 6. An orthographic projection of the magnetoresistive sensing unit string in the X-Y plane is located in an orthographic projection of the hydrogen sensing layer 1 in the X-Y plane. A long axis direction of the magnetoresistive sensing unit is the Y-axis direction and a short axis direction is the X-axis direction. It is understandable that a relative positional relationship between the non-hydrogen sensing layer and the reference magnetoresistive sensing unit string is similar to that in FIG. 6, and will not be repeated here.

As shown in FIG. 6, if the magnetoresistive sensing unit string and the hydrogen sensing layer 1 are projected into the same X-Y plane, the magnetoresistive sensing unit string is located in the hydrogen sensing layer 1 in the X-Y plane. Optionally, in the X-Y plane, the magnetoresistive sensing unit string is located on a Y-axis centerline 1-6 in the hydrogen sensing layer 1, and/or optionally, in the X-Y plane, the magnetoresistive sensing unit string is located in the hydrogen sensing layer 1 and is symmetrically arranged with the Y-axis centerline 1-6 as a symmetry axis. In another embodiment, if both the reference magnetoresistive sensing unit string and the non-hydrogen sensing layer are projected into the same X-Y plane, the reference magnetoresistive sensing unit string is located in the non-hydrogen sensing layer 1 in the X-Y plane. Optionally, in the X-Y plane, the magnetoresistive sensing unit string is located on a Y-axis centerline in the hydrogen sensing layer, and/or optionally, in the X-Y plane, the magnetoresistive sensing unit string is located in the hydrogen sensing layer and is symmetrically arranged with the Y-axis centerline as a symmetry axis.

It should be noted that, as shown in FIG. 7, the magnetoresistive sensing unit string in the X-Y plane may be located on the Y-axis centerline of the hydrogen sensing layer 1, and at the same time, and the reference magnetoresistive sensing unit string in the X-Y plane may be located on the Y-axis centerline of the non-hydrogen sensing layer 10. Alternatively, as shown in FIG. 8, the magnetoresistive sensing unit string in the X-Y plane may be located on the left side of the Y-axis centerline of the hydrogen sensing layer 1, and the reference magnetoresistive sensing unit string in the X-Y plane may be located at the same positions on the left side of the Y-axis centerline of the non-hydrogen sensing layer 10. Moreover, as shown in FIG. 8, the magnetoresistive sensing unit string in the X-Y plane may be located on the right side of the Y-axis centerline of the hydrogen sensing layer 1, and the reference magnetoresistive sensing unit string in the X-Y plane may be located at the same positions on the right side of the Y-axis centerline of the non-hydrogen sensing layer 10.

In this embodiment, magnetoresistive sensing units of the optional magnetoresistive sensing unit string and the reference magnetoresistive sensing unit string each include a pinning layer/an insulating layer/a free layer/a bias layer in sequence. The pinning layer is an anti-ferromagnetic layer/a ferromagnetic layer or an anti-ferromagnetic layer/a ferromagnetic layer/a metal conductive layer/a ferromagnetic layer. The bias layer is an anti-ferromagnetic layer or an anti-ferromagnetic/a ferromagnetic layer/a metal layer/a ferromagnetic layer, or a permanent magnet layer.

The hydrogen sensing layer 1 and the non-hydrogen sensing layer 10 respectively include a magnetoresistive sensing unit 2-3 and a reference magnetoresistive sensing unit 2-3-1 at positions corresponding to each other, such as positions on the Y-axis centerline 1-6, respectively include a magnetoresistive sensing unit 2-2 and a reference magnetoresistive sensing unit 2-2-1 at positions on the left side, and respectively include a magnetoresistive sensing unit 2-1 and a reference magnetoresistive sensing unit 2-1-1 at positions on the right side. Under the action of the background magnetic field and the combined action of hydrogen gas, the magnetization angle of the non-hydrogen sensing layer 10 will only be additionally deflected by $\Omega(b)$. In addition to be deflected by the angle $\Omega(b)$, the hydrogen sensing layer 1 will be further deflected by an angle $\Omega(H)$ due to the hydrogen gas, and will be reflected by a total angle of $\Omega(b+H)$. In this embodiment, a reference bridge structure may be selected to eliminate the effect of the background magnetic field $\Omega(b)$.

Regarding the structural diagram of the tunneling magnetoresistive sensor corresponding to the above background magnetic field elimination method, FIG. 7 is a half-bridge structure, including a half-bridge structure composed of the magnetoresistive sensing unit 2-3 and the reference magnetoresistive sensing unit 2-3-1 of the hydrogen sensing layer 1 and the non-hydrogen sensing layer at the same position. FIG. 8 is a full bridge structure, including a full bridge structure composed of two magnetoresistive sensing units 2-1 and 2-2 and two reference magnetoresistive sensing units 2-1-1 and 2-2-1 corresponding to the hydrogen sensing layer 1 and the non-hydrogen sensing layer 10 at the same position. It is understandable that the tunneling magnetoresistive sensor may be a quasi-bridge structure, a half-bridge structure, or a full-bridge structure.

Figure 9:
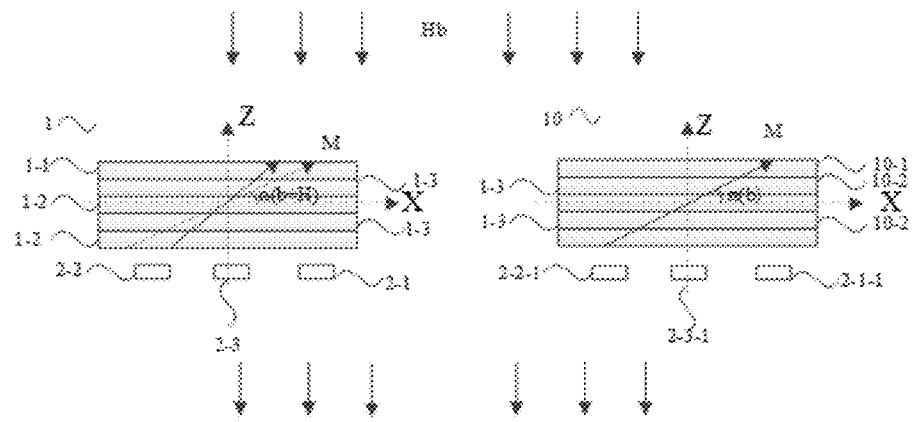
FIG. 9 is a second structural schematic diagram of a hydrogen sensing layer, a non-hydrogen sensing layer, and tunneling magnetoresistive sensors thereof according to an embodiment of the present disclosure.

As shown in FIG. 9, for the hydrogen sensing layer 1 and the non-hydrogen sensing layer 10, the hydrogen sensing layer 1 includes a palladium layer and a ferromagnetic layer 1-3, and the palladium layer includes a palladium layer 1-1 located in a cap layer and a palladium layer 1-2 located in an intermediate layer. The structure of the non-hydrogen sensing layer 10 is different from the structure of the hydrogen sensing layer 1 in that the non-hydrogen sensing layer 10 includes a non-palladium layer, where the non-palladium layer is a film layer made of a metal that does not react with hydrogen gas, such as Cu, Ti, and Ta. The palladium layer and the non-palladium layer are located in the same layer. It is understandable that the hydrogen sensing layer 1 and the non-hydrogen sensing layer 10 have the same geometric dimensions, including the thickness and the number of layers, to ensure that the orientation angles of the two ferromagnetic layers are consistent due to the influence of the background magnetic field, that is, the environmental magnetic field. Moreover, a reference bridge structure formed by connecting the magnetoresistive sensing unit string and the reference magnetoresistive sensing unit string at the same positions corresponding to those of the hydrogen sensing layer 1 and the non-hydrogen sensing layer 10, such as the middle position, the left position, and the right position, is similar to that in FIG. 7 and FIG. 8, which will not be repeated here.

Figure 10:
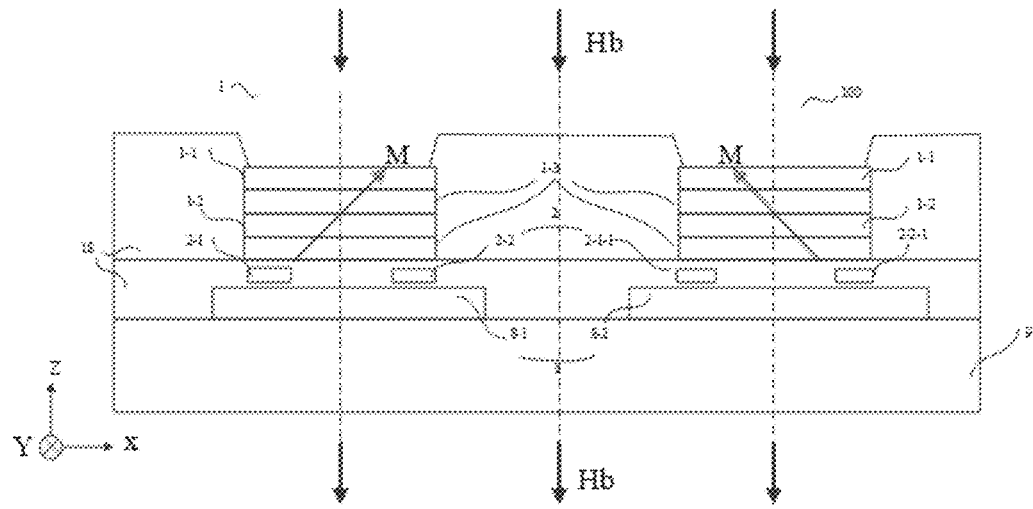
FIG. 10 is a schematic diagram of a hydrogen gas sensor according to an embodiment of the present disclosure.

For example, on the basis of the above technical solution, as shown in FIG. 10, the optional hydrogen sensing layer includes: a push hydrogen sensing layer 1 and a pull hydrogen sensing layer 100 that are electrically isolated on the same layer. When there is no external magnetic field, the push hydrogen sensing layer 1 has a magnetic moment in the direction of the positive X-axis, and the pull hydrogen sensing layer 100 has a magnetic moment in the direction of the negative X-axis.

Figure 11:
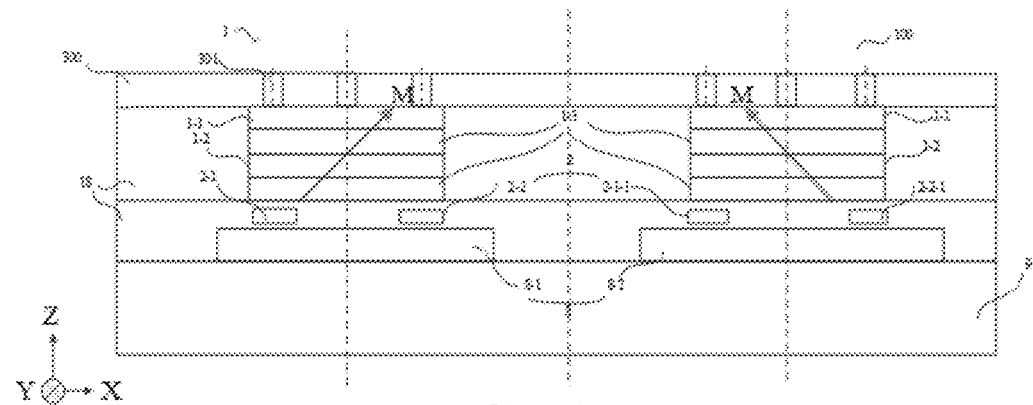
FIG. 11 is a schematic diagram of a hydrogen gas sensor according to an embodiment of the present disclosure.

As shown in FIG. 11, it also includes: a magnetic shielding layer 300 located on the hydrogen sensing layer. The magnetic shielding layer 300 includes at least one through hole 301. The palladium layer of the push hydrogen sensing layer 1 and the palladium layer of the pull hydrogen sensing layer 100 are in direct contact with the air through the at least one through hole 301. In this embodiment, the function of the magnetic shielding layer 300 is to eliminate the interference effect of the background magnetic field, while allowing the adsorption reaction between $H_2$ and the palladium layer, and the magnetic shielding layer 300 is a soft magnetic alloy material containing Fe, Co, or Ni. The palladium layer located in the cap layer may be denoted as 1-1, the palladium layer located in the intermediate layer may be denoted as 1-2, and the ferromagnetic layer is denoted as 1-3.

The optional tunneling magnetoresistive sensor 2 is a push-pull bridge sensor. The tunneling magnetoresistive sensor 2 includes a push arm and a pull arm. The push arm includes a push magnetoresistive sensing unit string, and the pull arm includes a pull magnetoresistive sensing unit string. Magnetic field sensitive directions of the push magnetoresistive sensing unit string and the pull magnetoresistive sensing unit string are both the X axis direction. The push hydrogen sensing layer and the pull hydrogen sensing layer are both strip shaped, a long axis of the strip is the Y-axis direction, and a short axis of the strip is the X-axis direction. In the X-Y plane, an orthographic projection of the push magnetoresistive sensing unit string is located on the Y-axis centerline in the strip of the push hydrogen sensing layer, and/or an orthographic projection of the push magnetoresistive sensing unit string is located at the same positions on both sides of the Y-axis centerline within the strip of the push hydrogen sensing layer. In the X-Y plane, an orthographic projection of the pull magnetoresistive sensing unit string is located on the Y-axis centerline in the strip of the pull hydrogen sensing layer, and/or an orthographic projection of the pull magnetoresistive sensing unit string is located at the same positions on both sides of the Y-axis centerline within the strip of the pull hydrogen sensing layer. The push magnetoresistive sensing unit string and the pull magnetoresistive sensing unit string are arranged in the same way. The push hydrogen sensing layer is magnetically coupled to the push arm and magnetically isolated from the pull arm. The pull hydrogen sensing layer is magnetically coupled to the pull arm and magnetically isolated from the push arm.

In this embodiment, the relative positional relationship between the push hydrogen sensing layer 1 and the push magnetoresistive sensing unit string may be obtained with reference to FIG. 6, and the relative positional relationship between the pull hydrogen sensing layer 100 and the pull magnetoresistive sensing unit string is similar thereto. The push magnetoresistive sensing unit string includes 2-1 and 2-2, the pull magnetoresistive sensing unit string includes 2-1-1 and 2-2-1, the push hydrogen sensing layer 1 is located above the push magnetoresistive sensing unit string 2-1 and 2-2, and the pull hydrogen sensing layer 100 is located above the pull magnetoresistive sensing unit string 2-1-1 and 2-2-1. The electrical isolation layer 18 is located between the push hydrogen sensing layer 1, the pull hydrogen sensing layer 100, and the tunneling magnetoresistive sensor 2, so as to realize the isolation of the hydrogen gas environment and the electric power supply environment, and avoid unnecessary explosions. It should be pointed out that surfaces of the push hydrogen sensing layer 1 and the hydrogen sensing layer 100 are both exposed to air.

In actual operation, due to the existence of the background magnetic field Hb and the bias of the magnetic moment generated by $H_2$ and the palladium in the push hydrogen sensing layer 1 and the pull hydrogen sensing layer 100, the push-pull bridge magnetoresistive sensor 2 collects the magnetic field signals of the push hydrogen sensing layer 1 and the pull hydrogen sensing layer 100 and generate output signals. The information of the background magnetic field is eliminated, the measurement of the $H_2$ concentration is realized, and physical isolation of the $H_2$ environment and the electrical environment is ensured.

Figure 12:
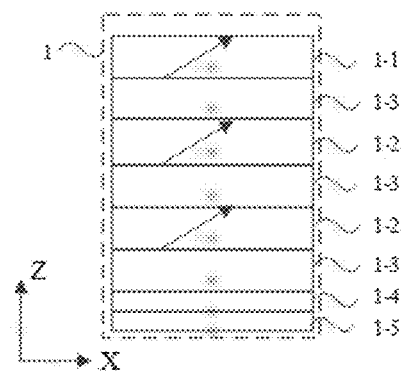
FIG. 12 is a schematic diagram of a hydrogen sensing layer according to an embodiment of the present disclosure.

For the hydrogen sensing layer described in any of the above embodiments, the optional hydrogen sensing layer shown in FIG. 12 further includes: a seed layer 1-5 and an isolation layer 1-4. The isolation layer 1-4 is located between the seed layer 1-5 and the multi-layer thin film structure of [palladium layer/ferromagnetic layer]n, and the orientation angle of the magnetization intensity of the ferromagnetic layer varies in a range of 10° to 80°. The isolation layer 1-4 is a Perpendicular Magnetic Anisotropy (PMA) layer. Optional, n=3, the palladium layer includes a palladium layer 1-1 arranged as the cap layer and a palladium layer 1-2 arranged as the intermediate layer. Arranging the palladium layer 1-1 as the cap layer can increase a contact area for reaction between the hydrogen gas and the palladium, and the ferromagnetic layer 1-3 is located between the palladium layers.

In this embodiment, under the action of $H_2$, the magnetic moment M of the ferromagnetic layer 1-3 is deflected in the X-Z plane, and the orientation angle in the X-axis direction is Ω. The ferromagnetic layer 1-3 has a thickness on the nanoscale, it can be regarded as a single domain structure, and therefore, the push hydrogen sensing layer 1 and the pull hydrogen sensing layer 100 may both be regarded as a magnet with the magnetic moment M, which generates a static magnetic field distribution in the surrounding space. The bottom of the hydrogen sensing layer is provided with magnetoresistive sensing unit strings 2-3, 2-2, and 2-1 at the position of the Y-axis centerline, the left position, and the right position, respectively, so as to realize the test of the static magnetic field, deduce the orientation angle of the magnetic moment M, and finally measure the $H_2$ concentration.

Figure 13:
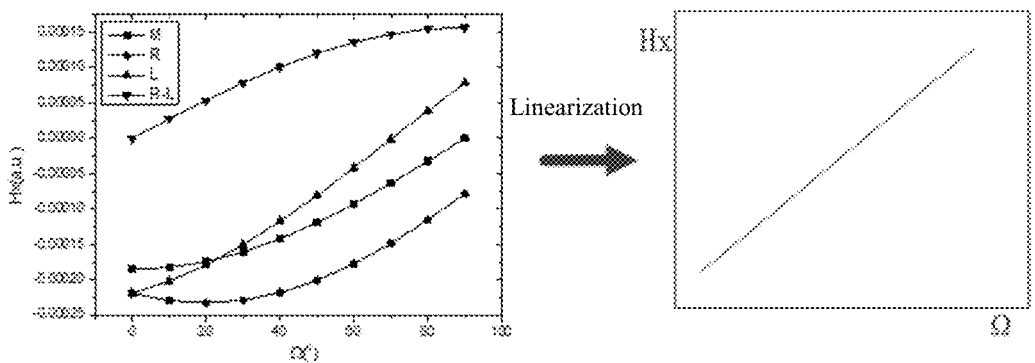
FIG. 13 is a linear conversion diagram of a relationship between a static magnetic field and an orientation angle of an X-axis of a magnetic moment of a hydrogen sensing layer at a position of a tunneling magnetoresistive sensor according to an embodiment of the present disclosure.

FIG. 13 shows components of a static magnetic field in the X-axis direction at the center position, the left position, and the right position of the Y-axis centerline of the hydrogen sensing layer 1 when the orientation angle Ω of the magnetic moment M varies in a range of 0 to 90°, and a change of a static magnetic field difference R-L in the X-axis direction at the left and right positions with the orientation angle Ω. As can be seen, a change curve of the static magnetic field with the orientation angle Ω has a linear segment and a nonlinear segment. The nonlinear segment appears at a position of the magnetic field close to 0 or close to 90° with the orientation angle Ω, and can be compensated by an algorithm to achieve linearization in the full range, so as to achieve linear results of the magnetic field orientation angle Ω and the tunneling magnetoresistive sensor, and realize the measurement of $H_2$ concentration by the tunneling magnetoresistive sensor.

For the hydrogen gas sensor including a hydrogen sensing layer and a non-hydrogen sensing layer described in the above embodiments.

Optionally, it further includes: a bias coil. A film layer where the bias coil is located is located between the substrate and the hydrogen sensing layer, the bias coil is located directly above or below the tunneling magnetoresistive sensor, and the bias coil is a spiral coil. For a bias magnetic field in the X-axial direction or the Y-axis direction, a plane where the bias coil is located includes a first bias region and a second bias region. The first bias region and the second bias region are respectively provided with N straight-line segments arranged in parallel and having the same electric current direction, where N is an integer greater than or equal to 1. The electric currents of the straight-line segments in the first bias region and the second bias region are in the same direction or in opposite directions, the hydrogen sensing layer is evenly distributed in the first bias region, and the non-hydrogen sensing layer is evenly distributed in the second bias region. For the bias magnetic field in the Z-axis direction, the plane where the bias coil is located includes a central bias region, and the central bias region is provided with 2M straight-line segments with the same number that are symmetrical arranged and have symmetrical and opposite electric current directions, where M is an integer greater than or equal to 1. The hydrogen sensing layer and the non-hydrogen sensing layer are arranged in the central bias region and arranged symmetrically. The electric current directions of the straight-line segments arranged corresponding to the hydrogen sensing layer are symmetrical and opposite, the electric current directions of the straight-line segments arranged corresponding to the non-hydrogen sensing layer are symmetrical and opposite, and the electric current directions are all perpendicular to the Y-axis centerline.

Optionally, it further includes: a permanent magnet bias layer. For the bias magnetic field in the X-axis direction or the Y-axis direction, the permanent magnet bias layer includes at least two permanent magnet bars arranged in parallel. The permanent magnet bars are located on both sides of the hydrogen sensing layer and on both sides of the non-hydrogen sensing layer. A bias magnetic field in the X-axis direction or a bias magnetic field in the Y-axis direction is generated between adjacent permanent magnet bars. For the bias magnetic field in the Z-axis direction, the permanent magnet bias layer includes a permanent magnet bar, which is located below the substrate. The hydrogen sensing layer and the non-hydrogen sensing layer are located in two regions of the permanent magnet bars with the same magnetic field components in the Z-axis direction, respectively. The hydrogen sensing layer and the non-hydrogen sensing layer are located in two regions of the permanent magnet bars with the symmetrical and opposite magnetic field components in the Y-axis direction.

In the hydrogen gas sensor as described above, the presence of a magnetic domain causes the dispersion of magnetic moments of the hydrogen sensing layer and the non-hydrogen sensing layer. In this embodiment, the magnetic moment dispersion caused by the magnetic domain is eliminated by the bias magnetic field, or it is used to saturate the hydrogen sensing layer and the non-hydrogen sensing layer under ferromagnetic resonance conditions to change the resonance frequency. Arranging the bias coil and arranging the permanent magnet bar are both solutions.

For the solution of arranging the bias coil to eliminate the magnetic moment dispersion caused by the magnetic domain. The bias coil can be used for generating a bias magnetic field, which in turn can dynamically excite a magnetic field as well as a microwave excitation signal.

Figure 14:
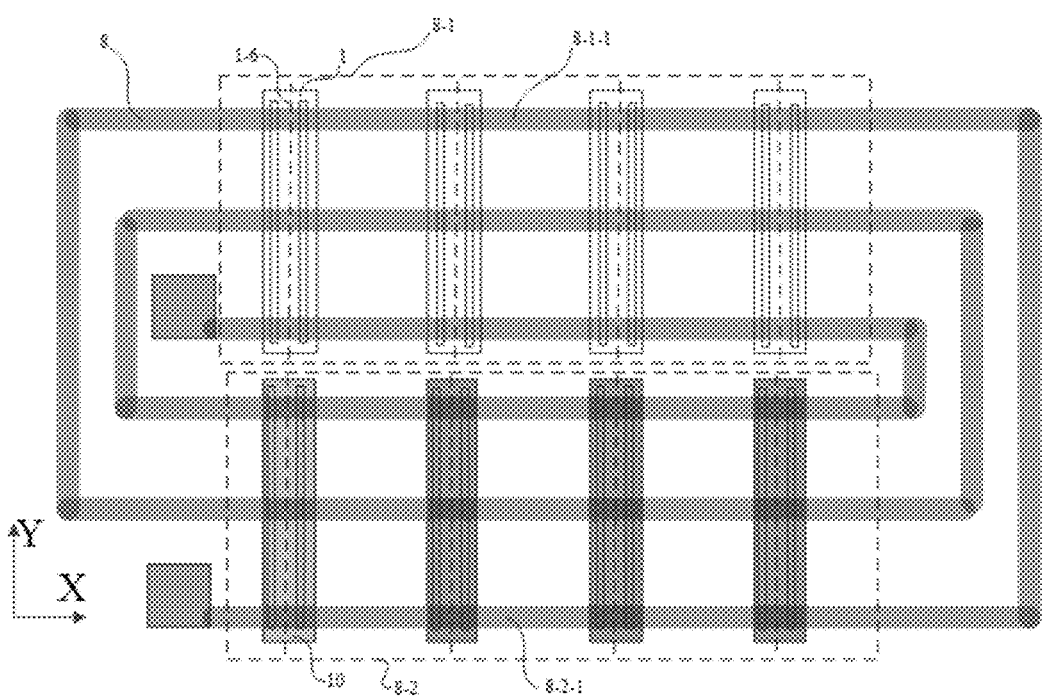
FIG. 14 is a schematic diagram of distribution of a spiral coil and tunneling magnetoresistive sensors according to an embodiment of the present disclosure.

Referring to FIG. 14, a spiral coil 8 is used for realizing the bias magnetic field. The drawing shows the distribution of the hydrogen sensing layer 1 and the non-hydrogen sensing layer 10 on the spiral coil 8 when a bias magnetic field Hy in the Y-axis direction is used. The hydrogen sensing layer 1 extends in the Y-axis direction, and a plurality of hydrogen sensing layers 1 are arranged in the X-axis direction. The non-hydrogen sensing layer 10 extends in the Y-axis direction, and the plurality of non-hydrogen sensing layers 10 are arranged in the X-axis direction. The hydrogen sensing layer 1 and the non-hydrogen sensing layer 10 are arranged in the Y-axis direction. The spiral coil 8 includes a plurality of straight-line segments extending in the Y-axis direction and a plurality of straight-line segments extending in the X-axis direction, where the plurality of straight-line segments extending in the Y-axis direction do not overlap the hydrogen sensing layer 1 and the non-hydrogen sensing layer 10, the plurality of straight-line segments extending in the X-axis direction overlap the hydrogen sensing layer 1 and the non-hydrogen sensing layer 10, and the plurality of straight-line segments extending in the Y-axis direction and the plurality of straight-line segments extending in the X-axis direction are electrically connected to form a spiral bias coil. Specifically, the spiral coil 8 includes two parallel straight-line segment regions 8-1 (i.e., the first bias region) and 8-2 (i.e., the second bias region), and the first and second bias regions are each composed of three parallel straight-line segments arranged at equal distances. The first bias region includes three straight-line segments 8-1-1, and the second bias region includes three straight-line segments 8-2-1. The electric current directions of the two bias regions are opposite, and the Y-axis centerlines 1-6 of the hydrogen sensing layer 1 and the non-hydrogen sensing layer 10 are both perpendicular to the electric current direction. Specifically, the hydrogen sensing layers 1 are uniformly distributed in the parallel straight-line segment region 8-1, and the non-hydrogen sensing layers 10 are uniformly distributed in the parallel straight-line segment region 8-2.

Figure 15:
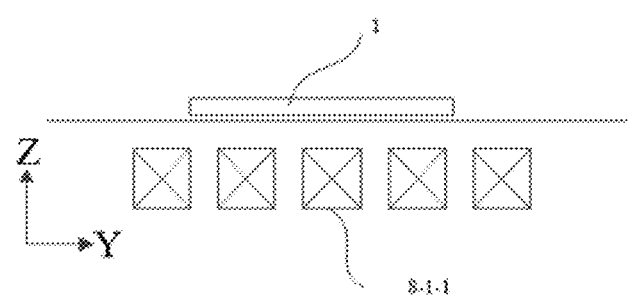
FIG. 15 is a schematic diagram of distribution of a spiral coil and a magnetoresistive sensing unit string according to an embodiment of the present disclosure.
Figure 16:
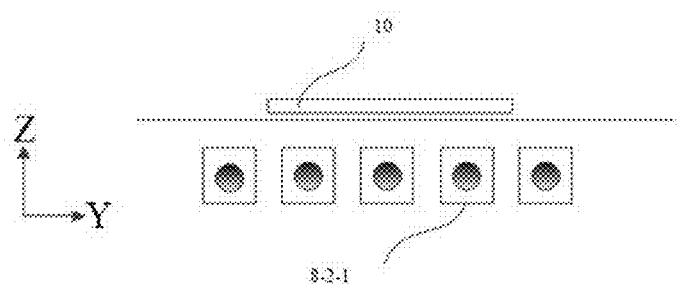
FIG. 16 is a schematic diagram of distribution of a spiral coil and a reference magnetoresistive sensing unit string according to an embodiment of the present disclosure.
Figure 17:
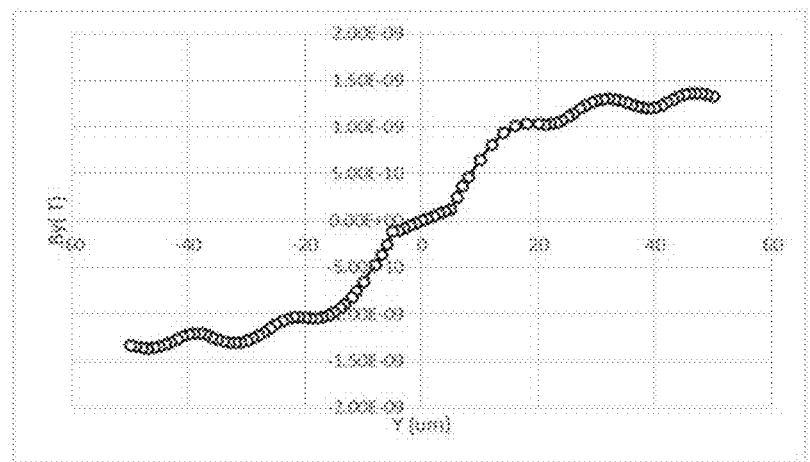
FIG. 17 is a bias magnetic field distribution diagram of a spiral coil biased in a Y-axis direction in a tunneling magnetoresistive sensor according to an embodiment of the present disclosure.

FIG. 15 is a cross-sectional view of the spiral coil and the hydrogen sensing layer 1, and FIG. 16 is a cross-sectional view of the spiral coil and the non-hydrogen sensing layer 10. Apparently, the electric current directions of the straight-line segments 8-1-1 and 8-2-1 of the spiral coil are opposite. The electric current direction of one bias region is the +X direction, and the circuit direction of the other bias region is the −X direction. The straight-line segment of the first bias region 8-1 is located directly under the hydrogen sensing layer 1, and the straight-line segment of the second bias region 8-2 is located directly under the non-hydrogen sensing layer 10. FIG. 17 shows the bias magnetic field in the Y-axis direction generated by the spiral coil 8. As can be seen, the bias magnetic field distributions in the Y-axis direction in the hydrogen sensing layer 1 and the non-hydrogen sensing layer 10 have the same amplitude and opposite directions.

Figure 18:
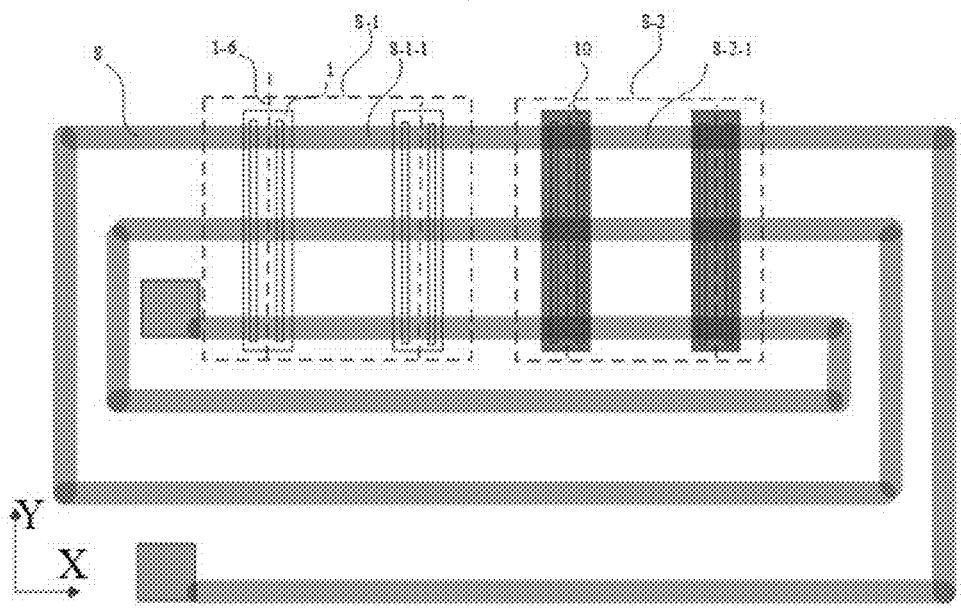
FIG. 18 is a schematic diagram of distribution of a spiral coil and a tunneling magnetoresistive sensor according to an embodiment of the present disclosure.

As shown in FIG. 18, the hydrogen sensing layer 1 extends in the Y-axis direction, and a plurality of hydrogen sensing layers 1 are arranged in the X-axis direction. The non-hydrogen sensing layer 10 extends in the Y-axis direction, and a plurality of non-hydrogen sensing layers 10 are arranged in the X-axis direction. The hydrogen sensing layer 1 and the non-hydrogen sensing layer 10 are arranged in the X-axis direction. The spiral coil 8 includes a plurality of straight-line segments extending in the Y-axis direction and a plurality of straight-line segments extending in the X-axis direction, where the plurality of straight-line segments extending in the Y-axis direction do not overlap the hydrogen sensing layer 1 and the non-hydrogen sensing layer 10, at least part of the straight-line segments extending in the X-axis direction overlap the hydrogen sensing layer 1 and the non-hydrogen sensing layer 10, and the plurality of straight-line segments extending in the Y-axis direction and the plurality of straight-line segments extending in the X-axis direction are electrically connected to form the spiral bias coil. In this embodiment, the hydrogen sensing layer 1 and the non-hydrogen sensing layer 10 are respectively placed in two parallel straight-line segment regions 8-1 and 8-2. The two parallel straight-line segment regions 8-1 and 8-2 are each composed of three identical parallel straight-line segments arranged at equal distances, that is, the area where the three parallel straight-line segments arranged at equal distances. That is, a region where three identical parallel straight-line segments arranged at equal distances overlap the hydrogen sensing layer 1 is the first bias region 8-1, and a region where the three identical parallel straight-line segments arranged at equal distances overlap the non-hydrogen sensing layer 10 is the second bias region 8-2. Therefore, the three parallel straight-line segments 8-1-1 and 8-2-1 each have the same electric current direction, and the electric current directions are perpendicular to the Y-axis centerline 1-6.

Figure 19:
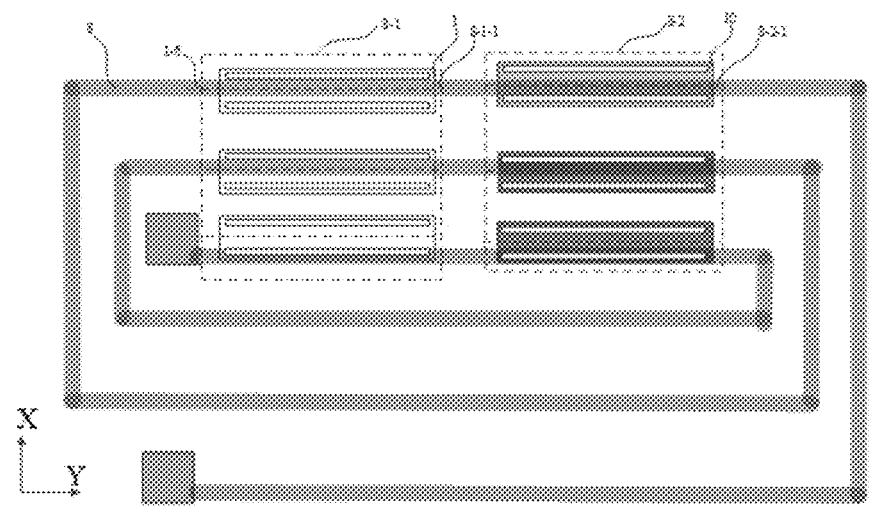
FIG. 19 is a schematic diagram of distribution of a spiral coil and a tunneling magnetoresistive sensor according to an embodiment of the present disclosure.

As shown in FIG. 19, it is a distribution diagram of the spiral coil 8, the hydrogen sensing layer 1, and the non-hydrogen sensing layer 10 with the bias magnetic field in the X-axis direction. The hydrogen sensing layer 1 extends in the Y-axis direction, and a plurality of hydrogen sensing layers 1 are arranged in the X-axis direction. The non-hydrogen sensing layer 10 extends in the Y-axis direction, and a plurality of non-hydrogen sensing layers 10 are arranged in the X-axis direction. The hydrogen sensing layer 1 and the non-hydrogen sensing layer 10 are arranged in the Y-axis direction. The spiral coil 8 includes a plurality of straight-line segments extending in the Y-axis direction and a plurality of straight-line segments extending in the X-axis direction. The plurality of straight-line segments extending in the X-axis direction do not overlap the hydrogen sensing layer 1 and the non-hydrogen sensing layer 10, at least part of the straight-line segments extending in the Y-axis direction overlap the hydrogen sensing layer 1 and the non-hydrogen sensing layer 10, and the plurality of straight-line segments extending in the Y-axis direction and the plurality of straight-line segments extending in the X-axis direction are electrically connected to form the spiral bias coil. In this embodiment, a difference from the bias magnetic field in the Y-axis direction is that the hydrogen sensing layer 1 and the non-hydrogen sensing layer 10 are rotated by 90°, so that the hydrogen sensing layer 1 and the non-hydrogen sensing layer 10 are placed in two parallel straight-line segment regions 8-1 and 8-2, respectively. The electric current directions of the parallel straight-line segments 8-1-1 and 8-2-1 are parallel to the Y-axis centerline 1-6, and the two parallel straight-line segment regions 8-1 and 8-2 are composed of three identical parallel straight-line segments arranged at equal distances. That is, a region where three identical parallel straight-line segments arranged at equal distances overlap the hydrogen sensing layer 1 is the first bias region 8-1, and a region where the three identical parallel straight-line segments arranged at equal distances overlap the non-hydrogen sensing layer 10 is the second bias region 8-2.

Figure 20:
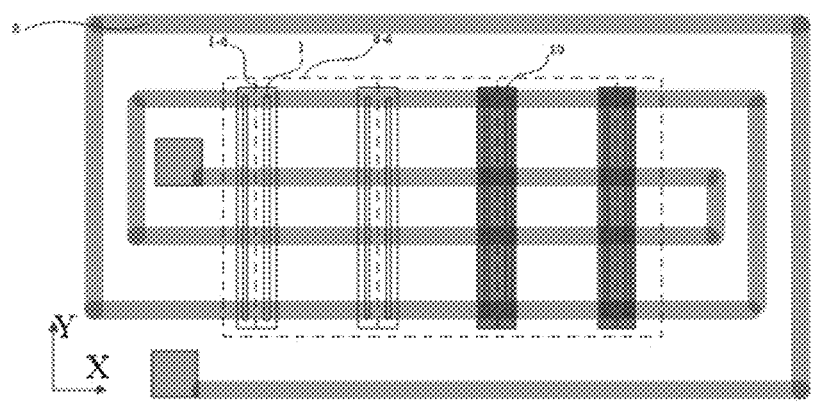
FIG. 20 is a schematic diagram of distribution of a spiral coil and a tunneling magnetoresistive sensor according to an embodiment of the present disclosure.

As shown in FIG. 20, it is a distribution diagram of the spiral coil 8, the hydrogen sensing layer 1, and the non-hydrogen sensing layer 10 with the bias magnetic field in the Z-axis direction. The hydrogen sensing layer 1 extends in the Y-axis direction, and a plurality of hydrogen sensing layers 1 are arranged in the X-axis direction. The non-hydrogen sensing layer 10 extends in the Y-axis direction, and a plurality of non-hydrogen sensing layers 10 are arranged in the X-axis direction. The hydrogen sensing layer 1 and the non-hydrogen sensing layer 10 are arranged in the X-axis direction. The spiral coil 8 includes a plurality of straight-line segments extending in the Y-axis direction and a plurality of straight-line segments extending in the X-axis direction. The plurality of straight-line segments extending in the Y-axis direction do not overlap the hydrogen sensing layer 1 and the non-hydrogen sensing layer 10, at least part of the straight-line segments extending in the X-axis direction overlap the hydrogen sensing layer 1 and the non-hydrogen sensing layer 10, and the plurality of straight-line segments extending in the Y-axis direction and the plurality of straight-line segments extending in the X-axis direction are electrically connected to form the spiral bias coil. In this embodiment, a difference from the bias magnetic field in the X-axis or Y-axis direction is that the hydrogen sensing layer 1 and the non-hydrogen sensing layer 10 are located in a middle region 8-4 (i.e., a central bias region) of the spiral coil 8. The middle region 8-4 includes two identical current straight-line segments in the positive X-axis direction and two current straight-line segments in the negative X-axis direction. The Y-axis centerlines 1-6 of the hydrogen sensing layer 1 and the non-hydrogen sensing layer 10 are both perpendicular to the electric current direction, and symmetrically span 4 straight-line segments, so that the spiral coil 8 can generate a magnetic field component in the Z-axis direction that is larger than that in other directions such as the Y-axis direction.

Figure 21:
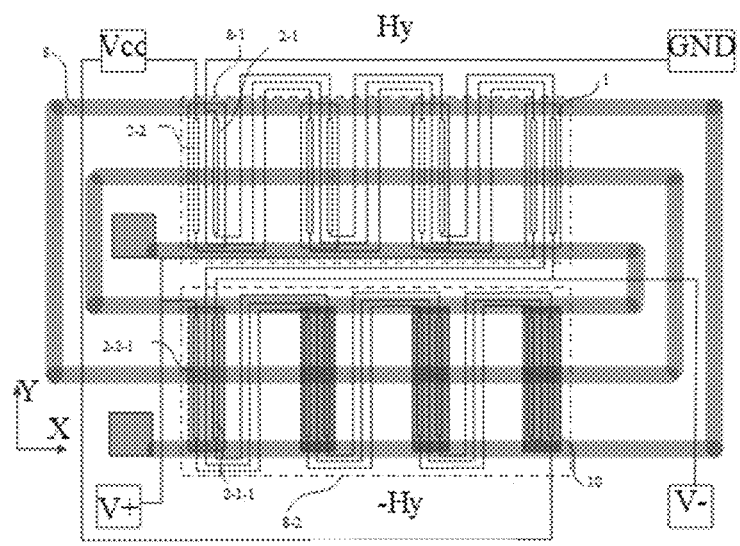
FIG. 21 is a schematic diagram of a spiral coil and a reference bridge tunneling magnetoresistive sensor according to an embodiment of the present disclosure.

As shown in FIG. 21, it is a schematic diagram of a hydrogen gas sensor utilizing reference bridge tunneling magnetoresistive sensors. In the spiral coil 8, the magnetoresistive sensing unit strings 2-1 and 2-2 of the hydrogen sensing layer 1 corresponding to the parallel straight-line segment region 8-1 and the reference magnetoresistive sensing unit strings 2-1-1 and 2-2-1 of the non-hydrogen sensing layer 10 corresponding to the parallel straight-line segment region 8-2 are electrically connected to form a reference full-bridge structure, and are connected to four pins of VCC, GND, V+, and V−.

As shown in FIG. 22, the principle of measuring hydrogen gas based on the hydrogen gas sensor of the above embodiment is that the hydrogen sensing layer 1 senses $H_2$ and the background magnetic field Hb, the non-hydrogen sensing layer 10 only senses the background magnetic field Hb, and the spiral coil 8 is used for applying the bias magnetic field. The magnetoresistive sensing unit strings 2-1 and 2-2 corresponding to the hydrogen sensing layer 1 and the reference magnetoresistive sensing unit strings 2-1-2 and 2-2-1 corresponding to the non-hydrogen sensing layer 10 constitute a reference bridge structure having an output end capable of outputting directly or through an analog front-end circuit.

As shown in FIG. 23a and FIG. 23b, a coil drive circuit is used for providing electric power to the spiral coil 8, and the spiral coil 8 dynamically excites the hydrogen sensing layer 1 and the non-hydrogen sensing layer 10 at the same time. A bridge output voltage of the reference bridge tunneling magnetoresistive sensor may be output directly or through the analog front-end circuit, and an induced voltage having a frequency and phase corresponding to those of the excitation signal is collected. Therefore, the coil drive circuit and the bridge output voltage of the reference bridge tunneling magnetoresistive sensor are jointly connected to a digital control and analysis circuit, for analyzing and processing the relationship between an excitation magnetic field signal He of the electric power supply of the spiral coil and a response signal of the tunneling magnetoresistive sensor, and outputting a voltage signal related to the pressure concentration. The excitation magnetic field signal He and a change in the magnetic flux B of the ferromagnetic layers in the hydrogen sensing layer and the non-hydrogen sensing layer measured by the tunneling magnetoresistive sensors may form a B-H curve. By extracting the remanence Br, or parameters such as the coercive force Hc, the magnetic permeability p, the saturation magnetic induction intensity Bs, and the saturation magnetic field Hs to realize the measurement of $H_2$ concentration.

Figure 24B:
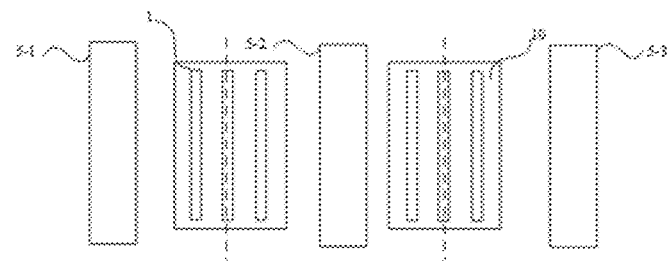
FIG. 24b is a schematic diagram of distribution of permanent magnet bars of a bias magnetic field in an X-axis direction according to an embodiment of the present disclosure.
Figure 25A:
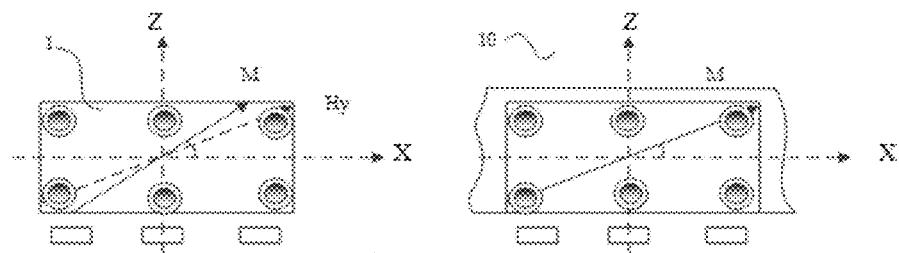
FIG. 25a is a magnetic moment deflection diagram of a bias magnetic field in a Y-axis direction according to an embodiment of the present disclosure.
Figure 25B:
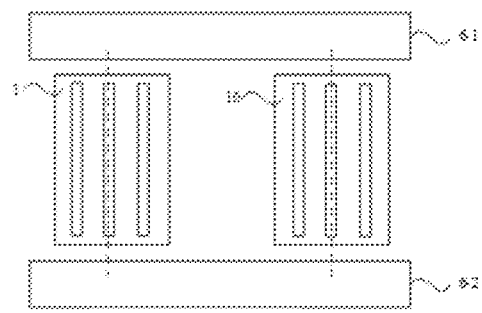
FIG. 25b is a schematic diagram of distribution of permanent magnet bars of a bias magnetic field in a Y-axis direction according to an embodiment of the present disclosure.
Figure 26A:
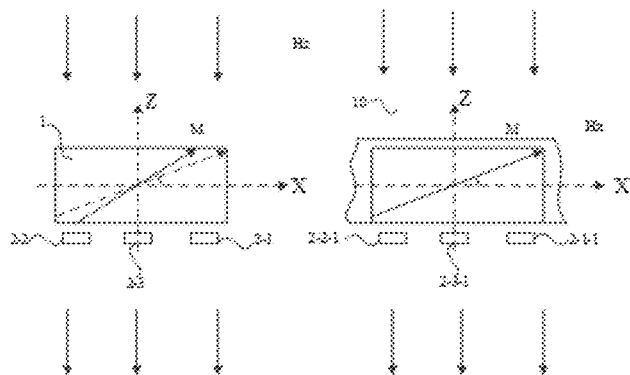
FIG. 26a is a magnetic moment deflection diagram of a magnetic field bias in a Z-axis direction according to an embodiment of the present disclosure.
Figure 26B:
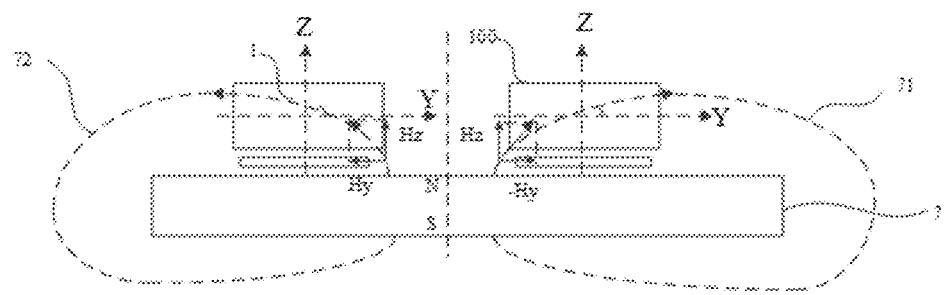
FIG. 26b is a schematic diagram of distribution of permanent magnet bars of a bias magnetic field in a Z-axis direction according to an embodiment of the present disclosure.

In order to eliminate the magnetic domains in the hydrogen sensing layer and the non-hydrogen sensing layer, so that the magnetic moment M in the ferromagnetic layer can be converted into the static magnetic field of the tunneling magnetoresistive sensor as much as possible, it is also necessary to use a magnetostatic bias function, and the static magnetic field may be in any of the X, Y, and Z directions. FIG. 24a shows a bias magnetic field Hx in the X-axis direction, and in actual production, permanent magnet bars 5-1, 5-2 and 5-3 shown in FIG. 24b may be prepared on the substrate, so that its magnetization direction is the X-axis direction. FIG. 25a shows a bias magnetic field Hy in the Y-axis direction, and in actual production, permanent magnet bars 6-1 and 6-2 shown in FIG. 25b may be prepared on the substrate, so that its magnetization direction is the Y-axis direction. FIG. 26a shows a bias magnetic field Hz in the Z-axis direction, and in actual production, a permanent magnet block 7 shown in FIG. 26b may be prepared on a lower surface of the substrate, so that its magnetization direction is the Z-direction, the hydrogen sensing layer 1 and the non-hydrogen sensing layer 10 are located symmetrically on both sides of the Z-axis centerline, respectively, and the permanent magnet horizontal magnetic field components are in the positive Y-axis and negative Y-axis directions, respectively.

Figure 27A:
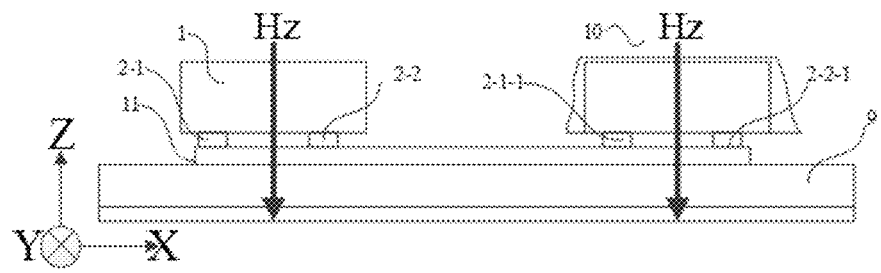
FIG. 27a is a front view of a reference magnetoresistive sensing unit bridge structure including ferromagnetic resonance microstrips according to an embodiment of the present disclosure.
Figure 27B:
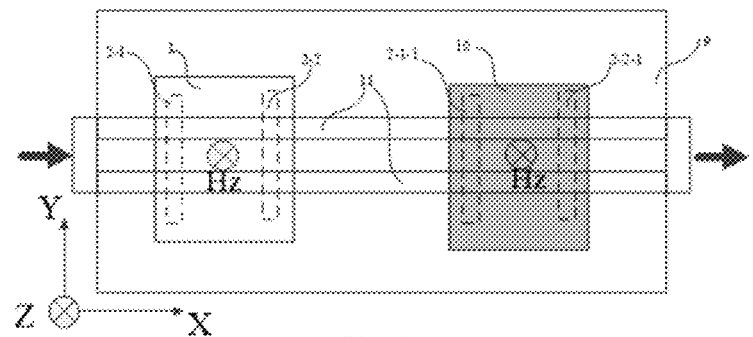
FIG. 27b is a top view of a microwave excitation magnetic field in a Y-axis direction according to an embodiment of the present disclosure.
Figure 27C:
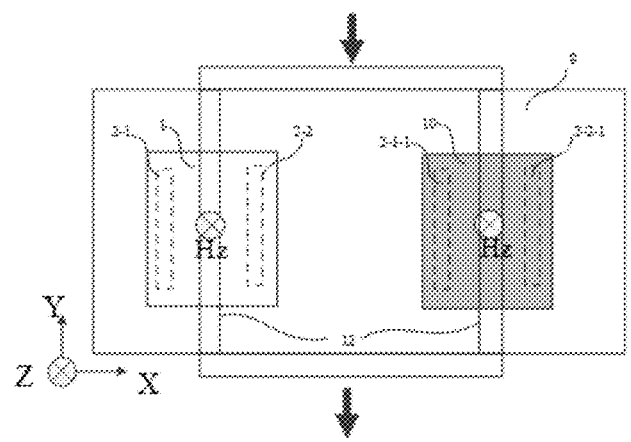
FIG. 27c is a top view of a microwave excitation magnetic field in an X-axis direction according to an embodiment of the present disclosure.

Optionally, the hydrogen gas sensor further includes a microstrip. The microstrip is a single-strip or a double-strip structure. The microstrip is located between the substrate and the tunneling magnetoresistive sensor, and both ends of the microstrip are connected to microwave ports and are connected to a microwave excitation power supply so that the bias magnetic field is in the Z-axis direction or the Y-axis direction. When the tunneling magnetoresistive sensor is a referenced bridge sensor, the microstrip is parallel or perpendicular to the Y-axis centerline. FIG. 27a to FIG. 27c are schematic diagrams of sensor structures for measuring the hydrogen gas concentration by a ferromagnetic resonance (FMR) method. Below the hydrogen sensing layer 1 and the non-hydrogen sensing layer 10, a microstrip 11 is used for transmitting a microwave excitation signal, and the microstrip 11 may be a single-strip or double-strip structure, and the microstrip 11 is directly fabricated on the substrate 9. The double-strip and single-strip cases are provided in this embodiment. At the same time, the magnetic field in the plane or perpendicular to the plane of the hydrogen sensing layer 1 and the non-hydrogen sensing layer 10 is used as the bias magnetic field. In this embodiment, the case of the vertical magnetic field Hz is provided. Microwave excitation magnetic fields in the hydrogen sensing layer 1 and the non-hydrogen sensing layer 10 provided in FIG. 27b are both in the Y-axis direction, and the microwave excitation magnetic fields in the hydrogen sensing layer 1 and the non-hydrogen sensing layer 10 provided in FIG. 27c are both in the X-axis direction.

Figure 28:
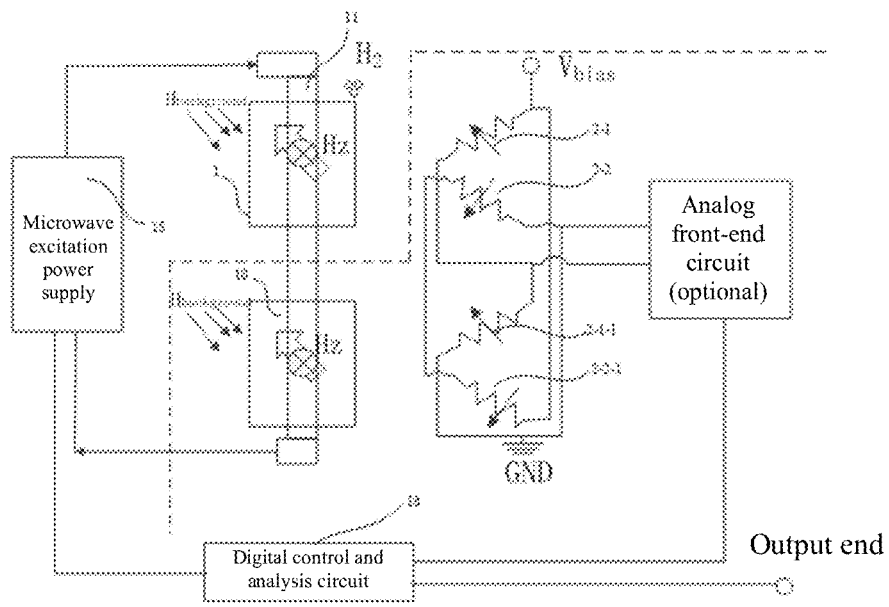
FIG. 28 is a diagram of hydrogen gas measurement of a reference magnetoresistive sensing unit bridge of a ferromagnetic resonance method according to an embodiment of the present disclosure.

As shown in FIG. 28, it is a schematic diagram of measuring the hydrogen gas concentration by a ferromagnetic resonance (FMR) method. A difference from the traditional analysis of input and output signals of microwave microstrips is that a reference full bridge structure formed by the magnetoresistive sensing unit strings 2-1 and 2-2 and the reference magnetoresistive sensing unit strings 2-1-1 and 2-2-1 corresponding to the hydrogen sensing layer 1 and the non-hydrogen sensing layer 10 is used for measuring a change in the magnetic flux density caused by the change in the magnetic permeability during a ferromagnetic resonance process in the ferromagnetic layer. The microwave excitation signal provided by the microwave excitation power supply 15 and the voltage signal output by the magnetoresistive sensor have a mutual relationship between frequency and phase, and therefore, the output of the sensor and the microwave excitation power supply 15 are transmitted to a digital control and analysis circuit 16 for processing, and then information related to the hydrogen gas content is output.

Figure 29:
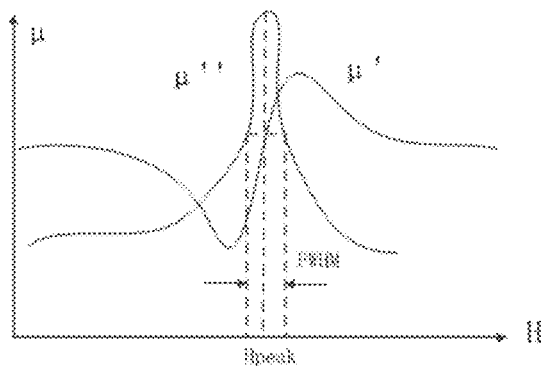
FIG. 29 is a graph showing variations in a magnetic permeability with a bias magnetic field according to an embodiment of the present disclosure.

As shown in FIG. 29, during the ferromagnetic resonance, the magnetic permeability is in the form of a complex number with a real part $\mu'$ and an imaginary part $\mu''$. In actual operation, the vertical bias magnetic field Hz is scanned within a certain range, and the microwave excitation power supply 15 performs frequency sweep within a certain frequency f range. Therefore, a magnetic spectrum obtained in a case that the bias magnetic field Hz of the magnetic permeability μ" or μ' is given or the change in the bias magnetic field Hz obtained in a case that the frequency f is given may be used for calibrating a relationship value at different hydrogen gas concentrations by taking a magnetic permeability resonance peak Hpeak or its full width at half maximum H (FWHM) as a parameter. A graph of the magnetic permeability varying along with the frequency f may also be used for calibrating the relationship value at different hydrogen gas concentrations by taking a magnetic permeability resonance peak fpeak or its full width at half maximum f (FWHM) as a parameter.

For the hydrogen gas sensor including the push hydrogen sensing layer and the pull hydrogen sensing layer described in the above embodiments.

Optionally, it further includes: a bias coil. A film layer where the bias coil is located is located between the substrate and the hydrogen sensing layer, the bias coil is located directly above or below the tunneling magnetoresistive sensor, and the bias coil is a spiral coil. For a bias magnetic field in the Y-axis direction, a plane where the bias coil is located includes a third bias region and a fourth bias region. The third bias region and the fourth bias region are respectively provided with P straight-line segments arranged in parallel and having the same electric current direction, where P is an integer greater than or equal to 1. The electric currents of the straight-line segments in the third bias region and the fourth bias region are in the same direction or in opposite directions, the push hydrogen sensing layer is evenly distributed in the third bias region, and the pull hydrogen sensing layer is evenly distributed in the fourth bias region. For the bias magnetic field in the Z-axis direction, the plane where the bias coil is located includes a central bias region, and the central bias region is provided with 2Q straight-line segments with the same number that are symmetrically arranged and have symmetrical and opposite electric current directions, where Q is an integer greater than or equal to 1. The push hydrogen sensing layer and the pull hydrogen sensing layer are arranged in the central bias region and arranged symmetrically. The electric current directions of the straight-line segments arranged corresponding to the push hydrogen sensing layer are symmetrical and opposite, the electric current directions of the straight-line segments arranged corresponding to the pull hydrogen sensing layer are symmetrical and opposite, and the electric current directions are all perpendicular to the Y-axis centerline.

Optionally, it further includes: a permanent magnet bias layer. For the bias magnetic field in the Y-axis direction, the permanent magnet bias layer includes at least two permanent magnet bars arranged in parallel. The permanent magnet bars are located on both sides of the push hydrogen sensing layer and on both sides of the pull hydrogen sensing layer. A bias magnetic field in the Y-axis direction is generated between adjacent permanent magnet bars. For the bias magnetic field in the Z-axis direction, the permanent magnet bias layer includes a permanent magnet bar, which is located below the substrate. The push hydrogen sensing layer and the pull hydrogen sensing layer are located in two regions of the permanent magnet bars with the same magnetic field components in the Z-axis direction, respectively. The push hydrogen sensing layer and the pull hydrogen sensing layer are located in two regions of the permanent magnet bars with the symmetrical and opposite magnetic field components in the Y-axis direction.

Figure 30:
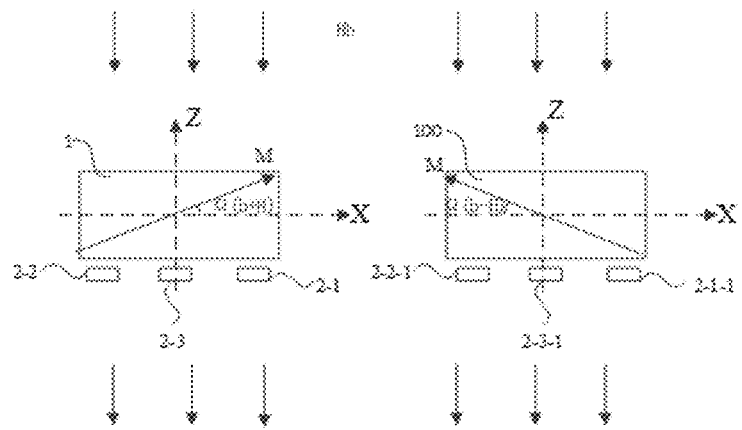
FIG. 30 is a structural diagram of a hydrogen sensing layer and a push-pull tunneling magnetoresistive sensor according to an embodiment of the present disclosure.

In the hydrogen gas sensor as described above, in addition to the push hydrogen sensing layer 1 biased in the positive X-axis direction as the hydrogen gas concentration increases, the hydrogen sensing layer further has a pull hydrogen sensing layer 100 biased reversely in the negative X-axis direction. As shown in FIG. 30, the push magnetoresistive sensing unit strings corresponding to the push hydrogen sensing layer 1 include 2-1, 2-2, and 2-3, and the pull magnetoresistive sensing unit strings corresponding to the pull hydrogen sensing layer 100 include 2-1-1, 2-2-2, and 2-3-1. Assuming that under the same hydrogen gas concentration conditions, the magnetic moment of the push hydrogen sensing layer 1 is deflected by an angle of +Ω, while the magnetic moment of the pull hydrogen sensing layer 100 is deflected by an angle of −Ω, and the push magnetoresistive sensing unit strings 2-1, 2-2, and 2-3 and the pull magnetoresistive sensing unit strings 2-1-1, 2-2-1, and 2-3-1 have opposite X-axis static magnetic field components. In addition, it is assumed that the environmental magnetic field Hb, the push hydrogen sensing layer 1 and the pull hydrogen sensing layer 100 have the same effect, and therefore, through the push-pull magnetoresistive bridge structure, the environmental magnetic field Hb can be eliminated, and the magnetic moment deflection and the static magnetic field caused by the hydrogen gas can be amplified at the same time.

FIG. 31*a* is a half-bridge bridge structural diagram of a push-pull magnetoresistive sensor, and FIG. 31*b* is a full-bridge bridge structural diagram of a push-pull magnetoresistive sensor. In addition, a quasi-bridge structure may also be formed, which will not be described here.

Optionally, methods for writing the positive X-axis direction magnetic moment of the push hydrogen sensing layer and the negative X-axis direction magnetic moment of the pull hydrogen sensing layer include any writing method of laser thermomagnetic writing, writing head writing, write coil writing, and permanent magnet block writing. A write coil is located between the substrate and the hydrogen sensing layer, where the write coil includes a first write wire along a Y-axis centerline of the push hydrogen sensing layer and having a positive Y-axis current direction and a second write wire along the Y-axis centerline of the pull hydrogen sensing layer and having a negative Y-axis current direction. The permanent magnet block is strip shaped and the permanent magnet block is located on a surface of the substrate on one side away from the hydrogen sensing layer, and the permanent magnet block has a magnetization direction in the Z-axis direction. The push hydrogen sensing layer and the pull hydrogen sensing layer are respectively located in regions on both sides of the Z-axis centerline of the permanent magnet block, and the regions on both sides have symmetrical and opposite magnetic field components in the X-axis direction.

FIG. 32*a* and FIG. 32*b* show the first writing method of the magnetic moment of the hydrogen sensing layer. The magnetic moment is written by using the laser thermomagnetic writing method. Specifically, in FIG. 32*a*, a laser beam 200 and magnetic field coils 201 and 202 are included. The laser beam 200 acts on the push hydrogen sensing layer 1 and heats it to the Curie temperature, and the magnetic field coils 201 and 202 generate a static magnetic field 203 in the positive X-axis direction. In FIG. 32*b*, the laser beam 200 acts on the pull hydrogen sensing layer 100 and heats it to the Curie temperature, and the magnetic field coils 201 and 202 generate a static magnetic field 204 in the negative X-axis direction. In this way, the magnetic moment in the positive X-axis direction and the magnetic moment in the negative X-axis direction are respectively obtained for the push hydrogen sensing layer 1 and the pull hydrogen sensing layer 100 by the laser thermomagnetic writing method.

Figure 33A:
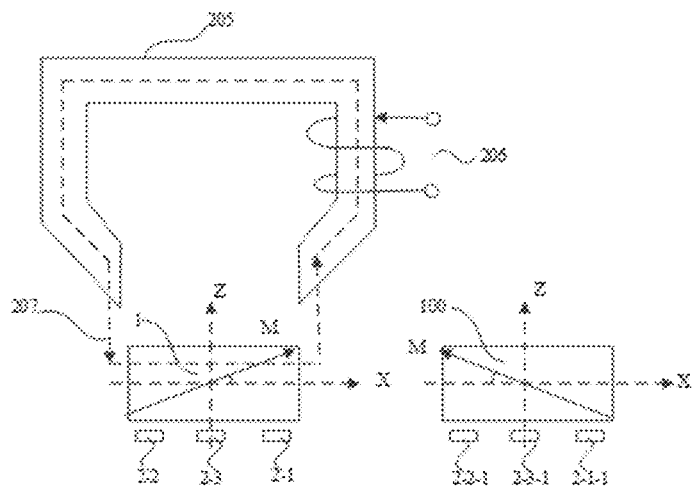
FIG. 33a is a schematic diagram of writing a magnetic moment of a push hydrogen sensing layer according to an embodiment of the present disclosure.
Figure 33B:
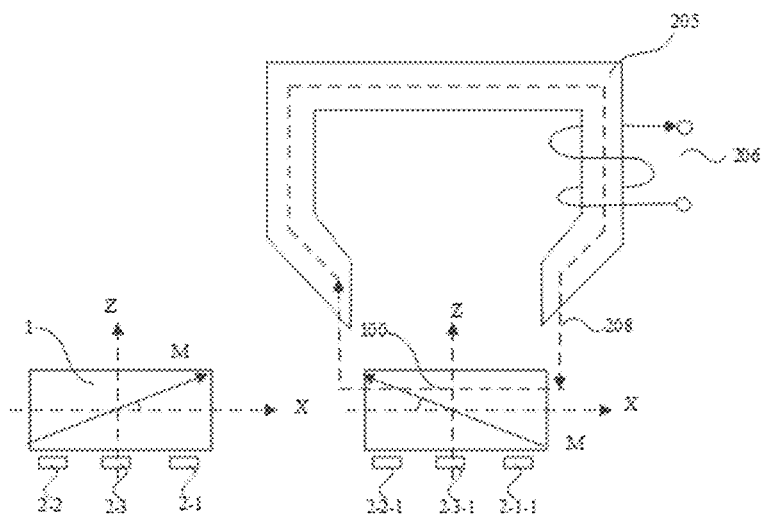
FIG. 33b is a schematic diagram of writing a magnetic moment of a pull hydrogen sensing layer according to an embodiment of the present disclosure.

FIG. 33a and FIG. 33b show the second writing method of the magnetic moment of the hydrogen sensing layer. The magnetic moment is directly written by the write head. The write head includes an open magnetic yoke 205 and an excitation coil 206. As shown in FIG. 33a, the write head generates a magnetic field in the positive X-axis direction above the push hydrogen sensing layer 1. As shown in FIG. 33b, the write head generates a magnetic field in the negative X-axis direction above the pull hydrogen sensing layer 100, which is implemented by changing the electric current direction of the excitation coil 106.

Figure 34A:
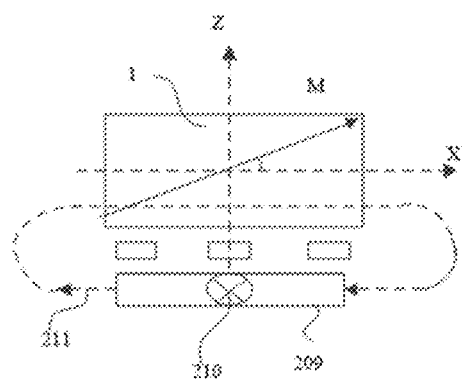
FIG. 34a is a schematic diagram of writing a magnetic moment of a push hydrogen sensing layer according to an embodiment of the present disclosure.
Figure 34B:
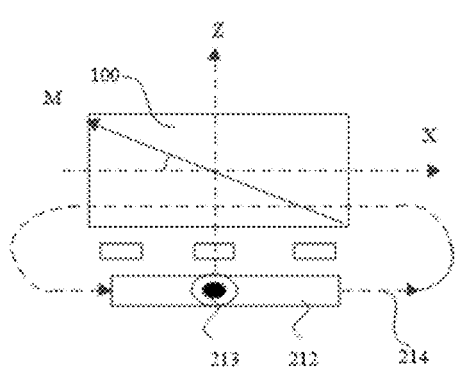
FIG. 34b is a schematic diagram of writing the magnetic moment of a pull hydrogen sensing layer according to an embodiment of the present disclosure.

FIG. 34a and FIG. 34b show the third writing method of the magnetic moment of the hydrogen sensing layer. The magnetic moment is written by fabricating a write coil on the substrate. Specifically, the write coil is located between the substrate and the hydrogen sensing layer. The write coil includes a first write wire in the direction of the Y-axis centerline of the push hydrogen sensing layer and having a positive Y-axis current direction and a second write wire in the direction of the Y-axis centerline of the pull hydrogen sensing layer and having a negative Y-axis current direction. As shown in the drawings, the first write wire 209 is formed below the push hydrogen sensing layer 1, and the second write wire 212 is formed below the pull hydrogen sensing layer 10. The first write wire 209 and the second write wire 212 are respectively parallel to the direction of the Y-axis centerline of the hydrogen sensing layer. A current direction 210 of the first write wire 209 is the positive Y-axis direction, and a current direction of the second write wire 212 is the negative Y-axis direction. Here, a current magnetic field 211 of the first write wire 209 is used to form a positive X-axis direction magnetic field in the push hydrogen sensing layer 1, and a current magnetic field 214 of the second write wire 212 is used to form a negative X-axis direction magnetic field in the pull hydrogen sensing layer 100. Thus, the magnetic moment writing of the push hydrogen sensing layer 1 and the pull hydrogen sensing layer 100 is completed.

Figure 35:
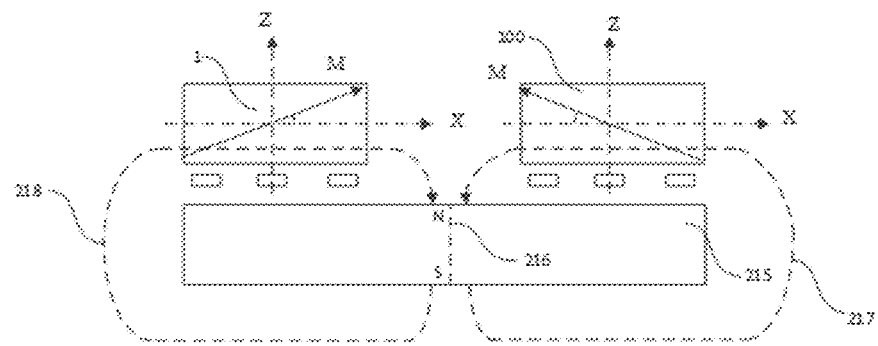
FIG. 35 is a schematic diagram of writing a magnetic moment of a push hydrogen sensing layer and a magnetic moment of a pull hydrogen sensing layer according to an embodiment of the present disclosure.

FIG. 35 shows the fourth writing method of the magnetic moment of the hydrogen sensing layer. The magnetic moment is written by placing a permanent magnet block 215 on the backside of the substrate. Specifically, the permanent magnet block 215 is strip shaped and the permanent magnet block 215 is located on a surface of the substrate on one side away from the hydrogen sensing layer. The permanent magnet block 215 has a magnetization direction in the Z-axis direction. The push hydrogen sensing layer 1 and the pull hydrogen sensing layer 100 are respectively located in regions on both sides of the Z-axis centerline of the permanent magnet block 215, and the regions on both sides have symmetrical and opposite magnetic field components in the X-axis direction. The magnetization direction of the permanent magnet block 215 is the Z-axis direction, and the push hydrogen sensing layer 1 and the pull hydrogen sensing layer 100 are placed symmetrically on both sides of a Z-axis centerline 216 of the permanent magnet block 215, so that a closed magnetic field 218 is formed between the permanent magnet block 215 and the push hydrogen sensing layer 1 located above, and a closed magnetic field 217 is further formed between the permanent magnet block 215 and the pull hydrogen sensing layer 100 located above. Moreover, the writing of the magnetic moments of the push hydrogen sensing layer 1 and the pull hydrogen sensing layer 100 is realized.

Figure 36:
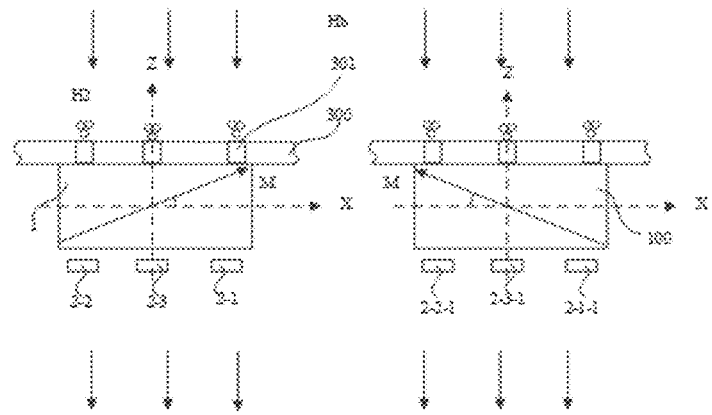
FIG. 36 is a structural diagram of a hydrogen sensing layer with a magnetic shielding layer and a tunneling magnetoresistive sensor according to an embodiment of the present disclosure.

FIG. 36 is a schematic diagram of a push-pull bridge type hydrogen gas sensor with a magnetic shielding layer 300. The push hydrogen sensing layer 1 and the pull hydrogen sensing layer 100 are covered by the magnetic shielding layer 300, and the magnetic shielding layer 300 is provided with a plurality of through holes 301 to allow hydrogen gas to enter the surface of the push hydrogen sensing layer 1 and the pull hydrogen sensing layer 100. The function of the magnetic shielding layer 300 is eliminating the interference effect of the background magnetic field, while allowing the reaction between $H_2$ and palladium layers. The magnetic shielding layer 300 is a soft magnetic alloy material containing Fe, Co, or Ni.

Figure 37:
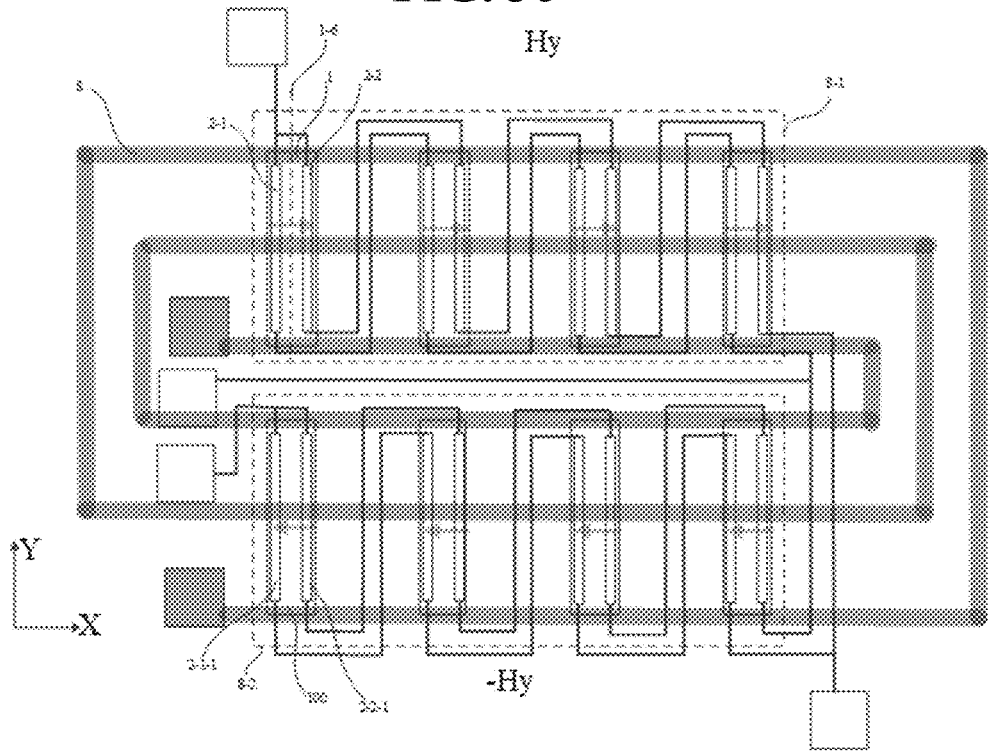
FIG. 37 is a diagram of distribution of a spiral coil biased in a Y-axis direction and a push-pull tunneling magnetoresistive sensor according to an embodiment of the present disclosure.

As shown in FIG. 37, the hydrogen gas sensor including the push hydrogen sensing layer 1 and the pull hydrogen sensing layer 100 can also be biased by a static magnetic field to eliminate the magnetic domain structure of the ferromagnetic layer. The push hydrogen sensing layer 1 and the pull hydrogen sensing layer 100 have magnetization directions in the positive and negative X-axis directions, and therefore, the push-pull structure of the hydrogen sensing layer will be destroyed if the X magnetic field is simply used. The tunneling magnetoresistive sensors have the same magnetic field sensitivity direction, and even if positive X and negative X magnetic fields are used, the tunneling magnetoresistive sensors will be in an abnormal working state. Therefore, only the magnetic field in the Y-axis direction or the bias magnetic field in the Z-axis direction can be selected.

FIG. 37 is a first distribution diagram of a bias coil in the Y-axis direction and the tunneling magnetoresistive sensors. The spiral coil includes a first bias region 8-1 and a second bias region 8-2, each bias region includes 3 parallel straight-line segments, and coil straight-line segments of the first bias region 8-1 and the second bias region 8-2 have opposite electric current directions. The push hydrogen sensing layer 1 and the push magnetoresistive sensing unit strings 2-1 and 2-2 are placed in the first bias region 8-1, and the Y-axis centerline 1-6 of the push hydrogen sensing layer 1 is perpendicular to the electric current direction. The pull hydrogen sensing layer 10 and the pull magnetoresistive sensing units 2-1-1 and 2-2-1 are placed in the second bias region 8-2.

Figure 38:
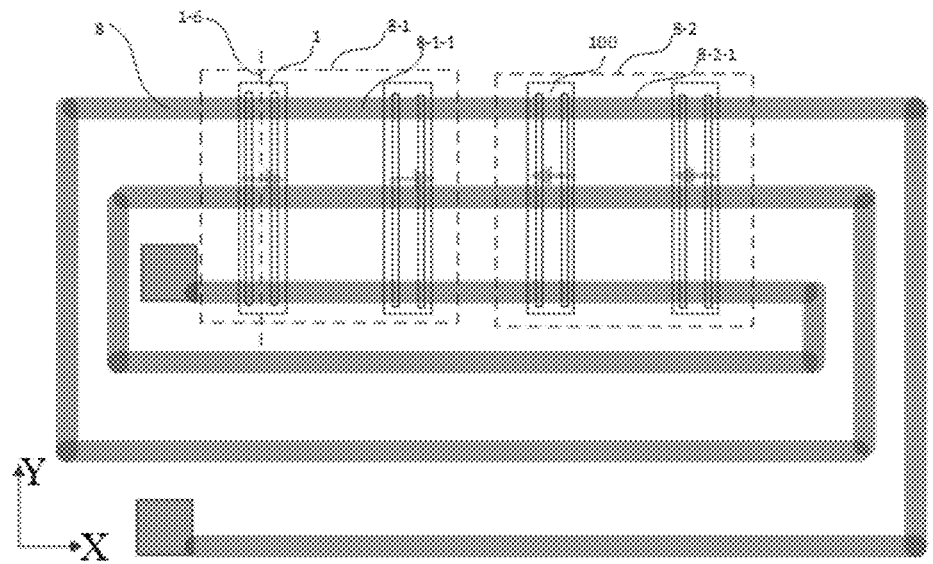
FIG. 38 is a diagram of distribution of a spiral coil biased in a Y-axis direction and a push-pull tunneling magnetoresistive sensor according to an embodiment of the present disclosure.

FIG. 38 is a second distribution diagram of a bias coil in the Y-axis direction and the tunneling magnetoresistive sensors. The spiral coil includes a first bias region 8-1 and a second bias region 8-2. A difference from FIG. 37 is that a straight-line segment 8-1-1 of the first bias region 8-1 and a straight-line segment 8-2-1 of the second bias region 8-2 have the same electric current direction, and the Y-axis centerline 1-6 of the hydrogen sensing layer is perpendicular to the electric current direction.

Figure 39:
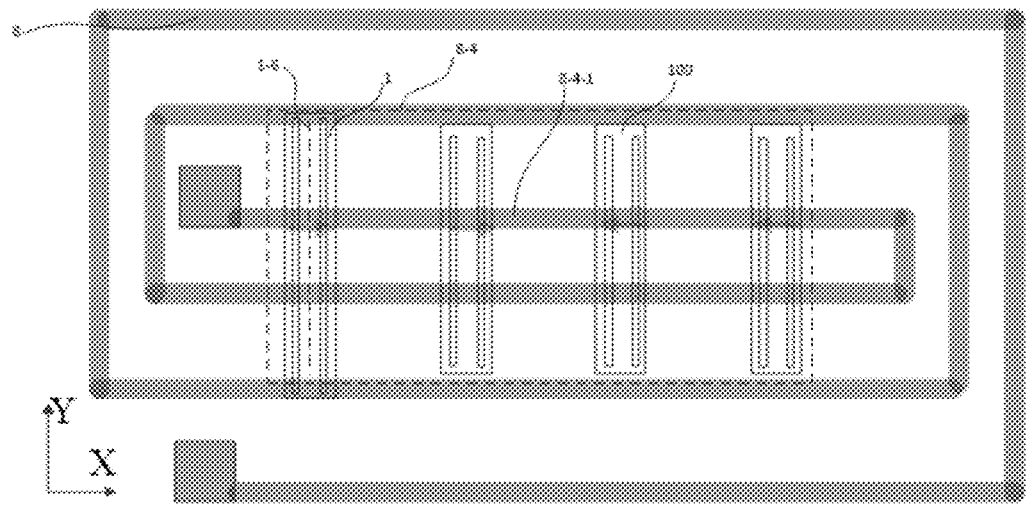
FIG. 39 is a diagram of distribution of a spiral coil biased in a Z-axis direction and a push-pull tunneling magnetoresistive sensor according to an embodiment of the present disclosure.

FIG. 39 is a distribution diagram of a Z-direction bias coil and the tunneling magnetoresistive sensors. The push hydrogen sensing layer 1 and the pull hydrogen sensing layer 100 are respectively located in a central bias region 8-4 of the spiral coil, and the central bias region 8-4 includes two straight wires 8-4 in the positive X-axis direction and two straight wires 8-4-1 in the negative X-axis direction. The Y-axis centerlines 1-6 of the push hydrogen sensing layer 1 and the pull hydrogen sensing layer 100 are perpendicular to the electric current direction, and symmetrically span the straight wire 8-4 in the positive X-axis direction and the straight wire 8-4-1 in the negative X-axis direction, so that the central bias region 8-4 generates a magnetic field in the Z-axis direction and magnetic fields in the positive Y-axis and negative Y-axis directions in the push hydrogen sensing layer 1 and the pull hydrogen sensing layer 100.

Figure 40A:
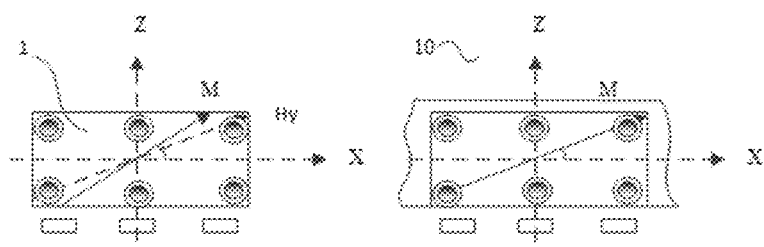
FIG. 40a is a magnetic moment deflection diagram of a bias magnetic field in a Y-axis direction according to an embodiment of the present disclosure.
Figure 40B:
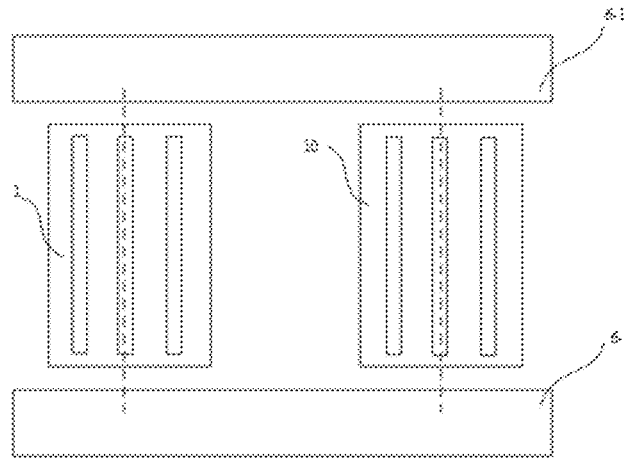
FIG. 40b is a diagram of distribution of permanent magnet bars biased in a magnetic field in a Y-axis direction according to an embodiment of the present disclosure.
Figure 41:
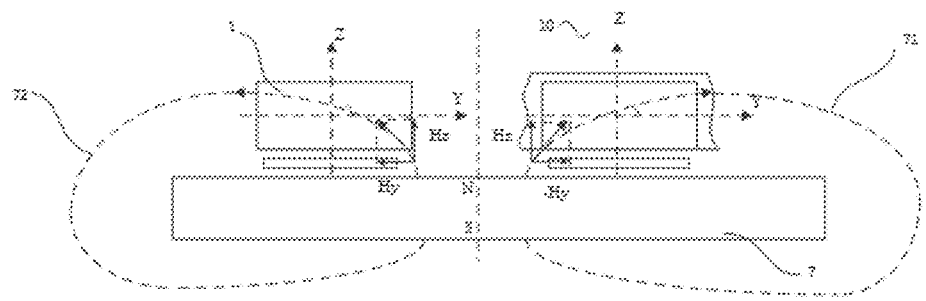
FIG. 41 is a magnetic field distribution diagram of permanent magnet bars in a Z-axis direction according to an embodiment of the present disclosure.

In this embodiment, a permanent magnet bar may optionally be used to generate the bias magnetic field. Specifically, as shown in FIG. 40*a*, the push hydrogen sensing layer 1 and the pull hydrogen sensing layer 100 sense the magnetic field in the Y-axis direction, respectively. As shown in FIG. 40*b*, a bias magnetic field in the Y-axis direction is generated between two parallel permanent magnet bars 6-1 and 6-2, and is located between the push hydrogen sensing layer 1 and the pull hydrogen sensing layer 100. FIG. 41 is a distribution diagram of a bias magnetic field in the Z-axis direction of the permanent magnet bar and the tunneling magnetoresistive sensors. The permanent magnet bar 7 is located below the tunneling magnetoresistive sensors, and has a magnetization direction in the Z-axis direction. The push hydrogen sensing layer 1 and the pull hydrogen sensing layer 100 are located symmetrically on both sides of a Z-axis centerline, respectively, so as to form two closed magnetic circuits 72 and 71. It should be pointed out that the magnetic circuits 72 and 71 formed by the permanent magnet bar 7 in the push hydrogen sensing layer 1 and the pull hydrogen sensing layer 100 are located on the Y-Z plane, and only have Y components except for Z components.

Figure 42:
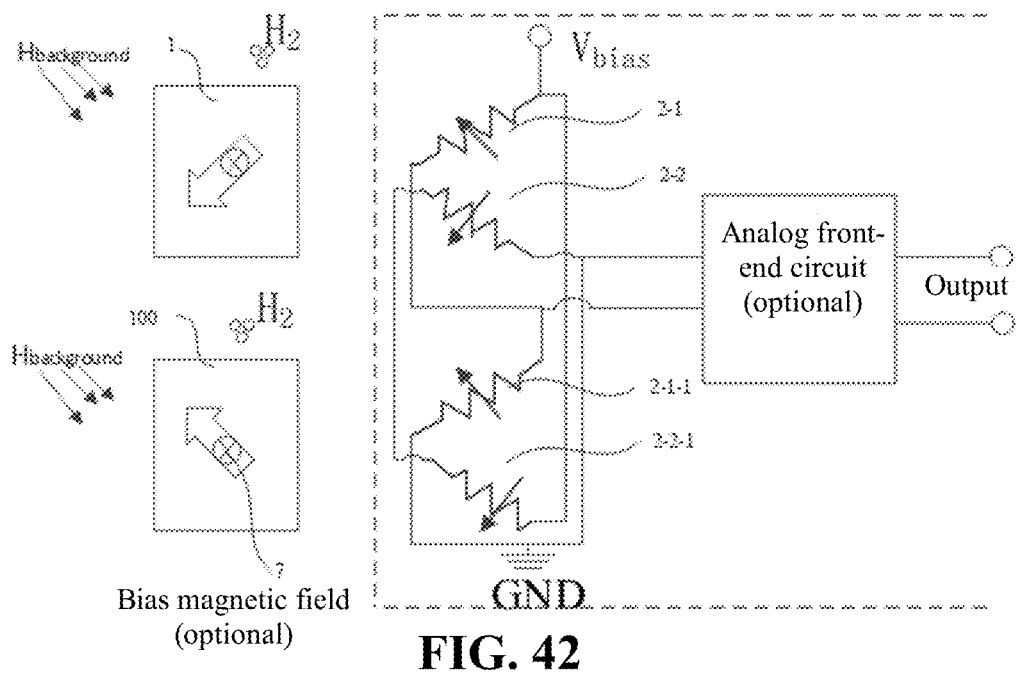
FIG. 42 is a schematic diagram of hydrogen gas measurement of a static magnetic field push-pull magnetoresistive sensing unit bridge according to an embodiment of the present disclosure.

FIG. 42 shows a hydrogen gas sensor utilizing tunneling magnetoresistive sensors structure biased by a static magnetic field. The measurement principle is that the push hydrogen sensing layer 1 and the pull hydrogen sensing layer 100 react with hydrogen gas respectively to form a reverse magnetic field. The reverse magnetic field acts on the push magnetoresistive sensing unit strings 2-1 and 2-2 and the pull magnetoresistive sensing unit strings 2-1-1 and 2-2-1 of the tunneling magnetoresistive sensors, an output terminal of a formed push-pull magnetoresistive sensing unit bridge outputs directly or outputs a voltage signal related to hydrogen gas through an analog front-end circuit. In addition, it can be realized by relying only on the magnetic moment of the hydrogen sensing layer or by applying a bias static magnetic field 7 at the same time, and the bias static magnetic field may be a spiral coil or a permanent magnet bar or both existing simultaneously.

FIG. 43*a* and FIG. 43*b* are schematic diagrams of dynamic hydrogen gas measurement of an electromagnetic coil of a push-pull bridge tunneling magnetoresistive sensor. In this embodiment, a coil drive circuit is used for providing electric power to the spiral coil 8, and the spiral coil 8 dynamically excites the push hydrogen sensing layer 1 and the pull hydrogen sensing layer 100 at the same time. An induced voltage having a frequency and phase corresponding to those of an excitation signal is collected by the push-pull bridge tunneling magnetoresistive sensor. The output voltage of the push-pull bridge tunneling magnetoresistive sensing unit bridge may be output directly or through the analog front-end circuit, and therefore, the coil drive circuit and the output voltage of the push-pull bridge tunneling magnetoresistive sensor bridge are jointly connected to the digital control and analysis circuit to analyze and process the relationship between the excitation magnetic field signal He of the spiral coil power supply and a response signal of the tunneling magnetoresistive sensor, and output a voltage signal related to the concentration of $H_2$. The change in the magnetic flux B of the ferromagnetic layers in the hydrogen sensing layer and the non-hydrogen sensing layer measured by the excitation magnetic field signal He and the tunneling magnetoresistive TMR may form a B-H curve. By extracting the remanence Br, or parameters such as the coercive force Hc, the magnetic permeability p, the saturation magnetic induction intensity Bs, and the saturation magnetic field Hs to realize the measurement of $H_2$ concentration. The difference between the push-pull bridge tunneling magnetoresistive sensor and the reference bridge tunneling magnetoresistive sensor is that the excitation magnetic field He can only be reversed in the Y or Z direction.

Optionally, the hydrogen gas sensor further includes: a microstrip. The microstrip is a single-strip or a double-strip structure. The microstrip is located between the substrate and the tunneling magnetoresistive sensor, and both ends of the microstrip are connected to the microwave ports and are connected to the microwave excitation power supply so that the bias magnetic field is in the Z-axis direction or the Y-axis direction. When the tunneling magnetoresistive sensor is a push-pull bridge sensor, the microstrip is perpendicular to the Y-axis direction centerline.

As shown in FIG. 44*a* and FIG. 44*b*, below the push hydrogen sensing layer 1 and the pull hydrogen sensing layer 100, a microstrip 11 is used for transmitting the microwave excitation signal, the microstrip 11 may be a single-strip or double-strip structure, and the microstrip 11 is directly fabricated on the substrate 9. This embodiment shows the double-strip situation, and as shown in FIG. 44*b*, the magnetic field in the plane of the push hydrogen sensing layer 1 and the pull hydrogen sensing layer 100 or perpendicular to the plane is used as the bias magnetic field. The case of the vertical magnetic field Hz is provided in this embodiment. In addition, the microwave excitation magnetic field shown above is in the Y-axis direction in both the push hydrogen sensing layer 1 and the pull hydrogen sensing layer 100, but cannot be in the X-axis direction.

FIG. 45*a* and FIG. 45*b* are schematic diagrams of measuring the hydrogen gas concentration by using a ferromagnetic resonance (FMR) method. A difference from the traditional analysis of the input and output signals of the microstrip is that this embodiment adopts a push-pull full-bridge structure composed of the push magnetoresistive sensing unit strings 2-1 and 2-2 and the pull magnetoresistive sensing unit strings 2-1-1 and 2-2-1 corresponding to the push hydrogen sensing layer 1 and the pull hydrogen sensing layer 100 to measure the change in magnetic flux density caused by the change in the magnetic permeability during ferromagnetic resonance in the ferromagnetic layer. The microwave excitation signal provided by the microwave excitation power supply 15 and the voltage signal output by the magnetoresistive sensor have a mutual relationship between frequency and phase, and therefore, the output of the tunneling magnetoresistive sensor and the microwave excitation power supply 15 are transmitted to the digital control and analysis circuit 16 for processing, and then information related to the hydrogen gas content is output. During the ferromagnetic resonance, the magnetic permeability is in the form of a complex number with a real part $\mu'$ and an imaginary part $\mu''$. In actual operation, the vertical bias magnetic field Hz is scanned within a certain range, and the microwave excitation power supply 15 performs frequency sweep within a certain frequency f range. Therefore, a magnetic spectrum may be obtained in a case that the bias magnetic field Hz of the magnetic permeability $\mu''$ or $\mu'$ is given, or the change diagram in the bias magnetic field Hz may be obtained in a case that the frequency f is given. FIG. 45 provides a graph of the magnetic permeability varying along with the bias magnetic field Hz, for calibrating a relationship value at different hydrogen gas concentrations by taking a magnetic permeability resonance peak Hpeak or its full width at half maximum H (FWHM) as a parameter.

A graph of the magnetic permeability varying along with the frequency f may also be used for calibrating the relationship value at different hydrogen gas concentrations by taking a magnetic permeability resonance peak fpeak or its full width at half maximum f (FWHM) as a parameter.

FIG. 46 shows changes of typical output parameter voltages and the hydrogen gas concentration, and these output parameters may be the output voltage signal of the tunneling magnetoresistive sensor bridge circuit, or may be a Br, Hc, u, Bs, or Hs value corresponding to the B-H loop of the corresponding excitation coil electromagnetic signal, or may be a peak Hpeak shift or a full width at half maximum H (FWHM) value of the resonance frequency of the magnetic permeability corresponding to the ferromagnetic resonance.

It should be noted that the above are only preferred embodiments of the present disclosure and applied technical principles. Those skilled in the art will understand that the present disclosure is not limited to the specific embodiments described herein, and various obvious changes, readjustments, combinations, and substitutions can be made by those skilled in the art without departing from the protection scope of the present disclosure. Therefore, although the present disclosure has been described in detail through the above embodiments, the present disclosure is not limited to the above embodiments, and can also include more other equivalent embodiments without departing from the concept of the present disclosure. The scope of the present disclosure is defined by the scope of the appended claims.

The invention claimed is:

1. A hydrogen gas sensor utilizing electrically isolated tunneling magnetoresistive sensing elements, comprising:
   a substrate in an X-Y plane, tunneling magnetoresistive sensors located on the substrate, and a hydrogen sensing layer located on the tunneling magnetoresistive sensors, the hydrogen sensing layer and the tunneling magnetoresistive sensor being electrically isolated from each other, and the hydrogen sensing layer comprising a multi-layer thin film structure of [palladium layer/ferromagnetic layer]n, wherein n is an integer greater than or equal to 1; and
   the palladium layers being used for adsorbing hydrogen in the air that causes a change in the orientation angle of a magnetic anisotropy field in each of the ferromagnetic layers along an X-axis direction in the X-Z plane, and the tunneling magnetoresistive sensors being used for detecting a magnetic field signal of the hydrogen sensing layer, wherein the magnetic signal determines the hydrogen gas concentration.

2. The hydrogen gas sensor according to claim 1, further comprising: a non-hydrogen sensing layer, wherein the non-hydrogen sensing layer is located on the tunneling magnetoresistive sensors, and the hydrogen sensing layer, the non-hydrogen sensing layer, and the tunneling magnetoresistive sensor are electrically isolated from one another;
   the non-hydrogen sensing layer is a multi-layer thin film structure of [non-palladium layer/ferromagnetic layer]n, or the non-hydrogen sensing layer comprises a multi-layer thin film structure of [palladium layer/ferromagnetic layer]n and a passivation layer covering the multi-layer thin film structure.

3. The hydrogen gas sensor according to claim 2, wherein the tunneling magnetoresistive sensor is a referenced bridge sensor, the tunneling magnetoresistive sensor comprises a sensitive bridge arm and a reference bridge arm, the sensitive bridge arm comprises a magnetoresistive sensing unit string, the reference bridge arm comprises a reference magnetoresistive sensing unit string, and magnetic field sensitive directions of the magnetoresistive sensing unit string and the reference magnetoresistive sensing unit string are both the X-axis direction;
   the hydrogen sensing layer and the non-hydrogen sensing layer are both strip shaped, a long axis of the strip is a Y-axis direction, and a short axis of the strip is the X-axis direction;
   in the X-Y plane, an orthographic projection of the magnetoresistive sensing unit string is located on a Y-axis centerline within the strip of the hydrogen sensing layer, and/or, an orthographic projection of the magnetoresistive sensing unit string is located at the same positions on both sides of the Y-axis centerline within the strip of the hydrogen sensing layer; in the X-Y plane, an orthographic projection of the reference magnetoresistive sensing unit string is located on a Y-axis centerline within the strip of the non-hydrogen sensing layer, and/or an orthographic projection of the reference magnetoresistive sensing unit string is located at the same positions on both sides of the Y-axis centerline within the strip of the non-hydrogen sensing layer, wherein the magnetoresistive sensing unit string and the reference magnetoresistive sensing unit string are arranged in the same way; and
   the hydrogen sensing layer is magnetically coupled to the sensitive bridge arm and magnetically isolated from the reference bridge arm, and the non-hydrogen sensing layer is magnetically isolated from the sensitive bridge arm and magnetically coupled to the reference bridge arm.

4. The hydrogen gas sensor according to claim 1, wherein the hydrogen sensing layer comprises: a push hydrogen sensing layer and a pull hydrogen sensing layer that are arranged to be electrically isolated in the same layer, and the push hydrogen sensing layer has a magnetic moment in a positive X-axis direction when there is no external magnetic field, and the pull hydrogen sensing layer has a magnetic moment in a negative X-axis direction when there is no external magnetic field;
   methods for writing the positive X-axis direction magnetic moment of the push hydrogen sensing layer and the negative X-axis direction magnetic moment of the pull hydrogen sensing layer comprise any writing method of laser thermomagnetic writing, writing head writing, write coil writing, and permanent magnet block writing;
   a write coil is located between the substrate and the hydrogen sensing layer, wherein the write coil comprises a first write wire along a Y-axis centerline of the push hydrogen sensing layer and having a positive Y-axis current direction and a second write wire along a Y-axis centerline of the pull hydrogen sensing layer and having a negative Y-axis current direction; and
   the permanent magnet block is strip shaped and the permanent magnet block is located on a surface of the substrate on one side away from the hydrogen sensing layer, the permanent magnet block has a magnetization direction in a Z-axis direction, the push hydrogen sensing layer and the pull hydrogen sensing layer are respectively located in regions on both sides of a Z-axis centerline of the permanent magnet block, and the regions on both sides have symmetrical and opposite magnetic field components in the X-axis direction.

5. The hydrogen gas sensor according to claim 4, further comprising: a magnetic shielding layer located on the hydrogen sensing layer, wherein the magnetic shielding layer comprises at least one through hole, and a palladium layer of the push hydrogen sensing layer and a palladium layer of the pull hydrogen sensing layer are in direct contact with the air through the at least one through hole.

6. The hydrogen gas sensor according to claim 4, wherein the tunneling magnetoresistive sensor is a push-pull bridge sensor, the tunneling magnetoresistive sensor comprises a push arm and a pull arm, the push arm comprises a push magnetoresistive sensing unit string, the pull arm comprises a pull magnetoresistive sensing unit string, and magnetic field sensitive directions of the push magnetoresistive sensing unit string and the pull magnetoresistive sensing unit string are both the X-axis direction;
the push hydrogen sensing layer and the pull hydrogen sensing layer are both strip shaped, a long axis of the strip is the Y-axis direction, and a short axis of the strip is the X-axis direction;
in the X-Y plane, an orthographic projection of the push magnetoresistive sensing unit string is located on the Y-axis centerline in the strip of the push hydrogen sensing layer, and/or an orthographic projection of the push magnetoresistive sensing unit string is located at the same positions on both sides of the Y-axis centerline within the strip of the push hydrogen sensing layer; in the X-Y plane, an orthographic projection of the pull magnetoresistive sensing unit string is located on the Y-axis centerline in the strip of the pull hydrogen sensing layer, and/or an orthographic projection of the pull magnetoresistive sensing unit string is located at the same positions on both sides of the Y-axis centerline within the strip of the pull hydrogen sensing layer, wherein the push magnetoresistive sensing unit string and the pull magnetoresistive sensing unit string are arranged in the same way; and
the push hydrogen sensing layer is magnetically coupled to the push arm and magnetically isolated from the pull arm, and the pull hydrogen sensing layer is magnetically coupled to the pull arm and magnetically isolated from the push arm.

7. The hydrogen gas sensor according to claim 2, further comprising: a bias coil, wherein a film layer where the bias coil is located is located between the substrate and the hydrogen sensing layer, the bias coil is located directly above or below the tunneling magnetoresistive sensor, and the bias coil is a spiral coil;
for a bias magnetic field in the X-axial direction or the Y-axis direction, a plane where the bias coil is located comprises a first bias region and a second bias region, the first bias region and the second bias region are respectively provided with N straight-line segments arranged in parallel and having the same electric current direction, wherein N is an integer greater than or equal to 1, the electric currents of the straight-line segments in the first bias region and the second bias region are in the same direction or in opposite directions, the hydrogen sensing layer is evenly distributed in the first bias region, and the non-hydrogen sensing layer is evenly distributed in the second bias region;
for a bias magnetic field in the Z-axis direction, the plane where the bias coil is located comprises a central bias region, and the central bias region is provided with 2M straight-line segments with the same number that are symmetrically arranged and have symmetrical and opposite electric current directions, wherein M is an integer greater than or equal to 1, the hydrogen sensing layer and the non-hydrogen sensing layer are arranged in the central bias region and arranged symmetrically, the electric current directions of the straight-line segments arranged corresponding to the hydrogen sensing layer are symmetrical and opposite, the electric current directions of the straight-line segments arranged corresponding to the non-hydrogen sensing layer are symmetrical and opposite, and the electric current directions are all perpendicular to the Y-axis centerline.

8. The hydrogen gas sensor according to claim 2, further comprising: a permanent magnet bias layer, wherein
for a bias magnetic field in the X-axis direction or the Y-axis direction, the permanent magnet bias layer comprises at least two permanent magnet bars arranged in parallel, the permanent magnet bars are located on both sides of the hydrogen sensing layer and on both sides of the non-hydrogen sensing layer, a bias magnetic field in the X-axis direction or a bias magnetic field in the Y-axis direction is generated between adjacent permanent magnet bars; and
for a bias magnetic field in the Z-axis direction, the permanent magnet bias layer comprises a permanent magnet bar, which is located below the substrate, the hydrogen sensing layer and the non-hydrogen sensing layer are located in two regions of the permanent magnet bars with the same magnetic field components in the Z-axis direction, respectively, and the hydrogen sensing layer and the non-hydrogen sensing layer are located in two regions of the permanent magnet bars with symmetrical and opposite magnetic field components in the Y-axis direction.

9. The hydrogen gas sensor according to claim 4, further comprising: a bias coil, wherein a film layer where the bias coil is located is located between the substrate and the hydrogen sensing layer, the bias coil is located directly above or below the tunneling magnetoresistive sensor, and the bias coil is a spiral coil;
for a bias magnetic field in the Y-axis direction, a plane where the bias coil is located comprises a third bias region and a fourth bias region, the third bias region and the fourth bias region are respectively provided with P straight-line segments arranged in parallel and having the same electric current direction, wherein P is an integer greater than or equal to 1, the electric currents of the straight-line segments in the third bias region and the fourth bias region are in the same direction or in opposite directions, the push hydrogen sensing layer is evenly distributed in the third bias region, and the pull hydrogen sensing layer is evenly distributed in the fourth bias region; and
for a bias magnetic field in the Z-axis direction, the plane where the bias coil is located comprises a central bias region, and the central bias region is provided with 2Q straight-line segments with the same number that are symmetrically arranged and have symmetrical and opposite electric current directions, wherein Q is an integer greater than or equal to 1, the push hydrogen sensing layer and the pull hydrogen sensing layer are arranged in the central bias region and arranged symmetrically; the electric current directions of the straight-line segments arranged corresponding to the push hydrogen sensing layer are symmetrical and opposite, the electric current directions of the straight-line segments arranged corresponding to the pull hydrogen sensing layer are symmetrical and opposite, and the electric current directions are all perpendicular to the Y-axis centerline.

10. The hydrogen gas sensor according to claim 4, further comprising: a permanent magnet bias layer; wherein
for a bias magnetic field in the Y-axis direction, the permanent magnet bias layer comprises at least two permanent magnet bars arranged in parallel, the permanent magnet bars are located on both sides of the push hydrogen sensing layer and on both sides of the pull hydrogen sensing layer, and the bias magnetic field in the Y-axis direction is generated between adjacent permanent magnet bars; and
for a bias magnetic field in the Z-axis direction, the permanent magnet bias layer comprises a permanent magnet bar, which is located below the substrate, the push hydrogen sensing layer and the pull hydrogen sensing layer are located in two regions of the permanent magnet bars with the same magnetic field components in the Z-axis direction, respectively, and the push hydrogen sensing layer and the pull hydrogen sensing layer are located in two regions of the permanent magnet bars with the symmetrical and opposite magnetic field components in the Y-axis direction.

11. The hydrogen gas sensor according to claim 2, further comprising: a microstrip, wherein the microstrip is a single-strip or a double-strip structure, the microstrip is located between the substrate and the tunneling magnetoresistive sensor, and both ends of the microstrip are connected to microwave ports and are connected to a microwave excitation power supply so that the bias magnetic field is in the Z-axis direction or the Y-axis direction.

12. The hydrogen gas sensor according to claim 11, wherein when the tunneling magnetoresistive sensor is a referenced bridge sensor, the microstrip is parallel or perpendicular to the direction of the Y-axis centerline; and
when the tunneling magnetoresistive sensor is a push-pull bridge sensor, the microstrip is perpendicular to the direction of the Y-axis centerline.

13. The hydrogen gas sensor according to claim 1, wherein the hydrogen sensing layer further comprises: a seed layer and an isolation layer, and the isolation layer is located between the seed layer and the multi-layer thin film structure of [palladium layer/ferromagnetic layer]n, and the orientation angle of the magnetization intensity of the ferromagnetic layer varies in a range of 10° to 80°.

* * * * *